(12) United States Patent
McMahon et al.

(10) Patent No.: US 11,407,988 B2
(45) Date of Patent: Aug. 9, 2022

(54) COMPOSITION AND USES THEREOF

(71) Applicant: UNIVERSITY COLLEGE DUBLIN NATIONAL UNIVERSITY OF IRELAND, DUBLIN, Dublin (IE)

(72) Inventors: Hilary McMahon, Dublin (IE); Regina O'Sullivan, Dublin (IE); Ana Herrero, Dublin (IE)

( * ) Notice: Subject to any disclaimer, the term of this patent is extended or adjusted under 35 U.S.C. 154(b) by 651 days.

(21) Appl. No.: 16/065,617

(22) PCT Filed: Dec. 23, 2016

(86) PCT No.: PCT/EP2016/082557
§ 371 (c)(1),
(2) Date: Jun. 22, 2018

(87) PCT Pub. No.: WO2017/109170
PCT Pub. Date: Jun. 29, 2017

(65) Prior Publication Data
US 2020/0370030 A1    Nov. 26, 2020

(30) Foreign Application Priority Data
Dec. 23, 2015 (GB) ...................... 1522814

(51) Int. Cl.
*C12N 9/52* (2006.01)
*A01N 25/06* (2006.01)
*A01N 63/50* (2020.01)

(52) U.S. Cl.
CPC .............. *C12N 9/52* (2013.01); *A01N 25/06* (2013.01); *A01N 63/50* (2020.01); *C12Y 304/21066* (2013.01)

(58) Field of Classification Search
None
See application file for complete search history.

(56) References Cited

FOREIGN PATENT DOCUMENTS

| WO | 98/59045 | 12/1998 | |
|---|---|---|---|
| WO | WO 98/59045 | * 12/1998 | ............... C12N 9/52 |
| WO | 2008057293 A2 | 5/2008 | |

OTHER PUBLICATIONS

Meloun et al., "Complete primary structure of thermitase from Thermoactinomyces vulgaris and its structural features related to the subtilisin-type proteinases", FEBS 2463 vol. 183 No. 2 pp. 195-200 (Year: 1985).*
Jorgensen et al.,"Recombinant expression of Laceyella sacchari thermitase in Lactococcus lactis", Protein Expression and Purification 92: 148-155 (Year: 2013).*
Jorgensen et al. Thermitase amino acid sequence ; GenBank Deposit ADL09141.1; downloaded Nov. 6, 2021. (Year: 2021).*
Meloun et al.: "Complete primary structure of thermitase from thermoactinomyces vulgaris and its structural features related to the subtilisin-type proteinases" FEBS Letters 1985 NL, vol. 183, No. 2, 1985, pp. 195-200.
Verma et al.: "Alkaline protease from *Thermoactinomyces* sp. RS1 mitigates industrial pollution.". Protoplasma May 2014. vol. 251. No. 3. May 2014 (May 2014). pp. 711-718.
PCT/EP2016/082557 International Search Report dated Mar. 28, 2017.
Muller-Hellwig et al.: "Biochemical evidence for the proteolytic degradation of infectious prion protein PrPsc in hamster brain homogenates by foodborne bacteria.".Systematic And Applied Microbiology Mar. 2006. vol. 29. No. 2. Mar. 2006 (Mar. 2006). pp. 165-171.

* cited by examiner

*Primary Examiner* — Anand U Desai

(57) ABSTRACT

The present invention relates to a composition for degrading prion material comprising a Thermitase. Such compositions may be formed in solution and are particularly suited to degrading prion material on medical equipment or in the environment due to the Thermitases mild pH range and activity at relatively low temperatures. The present invention also relates to novel proteases, methods for prion degradation, decontamination or disinfection and a kit of parts.

17 Claims, 16 Drawing Sheets

Specification includes a Sequence Listing.

*No 16 (Query; SEQ ID NO: 1) v's No 10 (Subject; SEQ ID NO: 4); mature*

| Score | Expect | Method | Identities | Positives | Gaps |
|---|---|---|---|---|---|
| 538 bits(1385) | 0.0 | Compositional matrix adjust. | 271/279(97%) | 276/279(98%) | 0/279(0%) |

```
Query .......    YTPNDPYFSSRQYGPQKIQAPQAWDIAEGSGVKIAIVDTGVQSNHPDLAGKVVGGWDFVD
               YTPNDPYFS+RQYGPQKIQAPQAWDI EGSG KIAIVDTGVQSNHPDLAGKVVGGWDFVD
Sbjct   1      YTPNDPYFSTRQYGPQKIQAPQAWDITEGSGAKIAIVDTGVQSNHPDLAGKVVGGWDFVD  60

Query   61     NDSTPQDGNGHGTHCAGIAAAVTNNSTGIAGTAPKASILAVRVLDNSGSGTWTAVANGIT
               NDSTPQDGNGHGTHCAGIAAAVTNNSTGIAGTAPKASILAVRVLDNSGSGTWTAVANGIT
Sbjct   61     NDSTPQDGNGHGTHCAGIAAAVTNNSTGIAGTAPKASILAVRVLDNSGSGTWTAVANGIT  120

Query   121    YAADQGAKVISLSLGGTVGNSGLQQAVDYAWNKGSVVVAAAGNAGNTAPNYPAYYSNAIA
               YAADQGA VISLSLGGTVGNSGLQQAV+YAWNKGSVVVAAAGNAGNTAP+YPAYYSNAIA
Sbjct   121    YAADQGADVISLSLGGTVGNSGLQQAVNYAWNKGSVVVAAAGNAGNTAPHYPAYYSNAIA  180

Query   181    VASTDQNDNKSSFSTYGSWVDVAAPGSSIYSTYPTSTYASLSGTSMATPHVAGVAGLLAS
               VASTDQNDNKSSFSTYGSWVDVAAPGSSIY+TYPTSTYASLSGTSMATPHVAGVAGLLAS
Sbjct   181    VASTDQNDNKSSFSTYGSWVDVAAPGSSIYATYPTSTYASLSGTSMATPHVAGVAGLLAS  240

Query   241    QGRSASNIRAAIENTADKISGTGTYWAKGRVNAYKAVQY  279
               QGRSASNIRAAIENTADKISGTG+YWAKGRVNAYKAVQY
Sbjct   241    QGRSASNIRAAIENTADKISGTGSYWAKGRVNAYKAVQY  279
```

Figure 11

*No 16 (Query; SEQ ID NO: 2) v's No 10 (Subject; SEQ ID NO: 5); Complete signal prodomain +mature*

| Score | Expect | Method | Identities | Positives | Gaps |
|---|---|---|---|---|---|
| 761 bits(1965) | 0.0 | Compositional matrix adjust. | 378/387(98%) | 384/387(99%) | 0/387(0%) |

```
Query   16     MKKRVSLIASFVLMASAALPSAIFAEEVDSQAGKLYAPGQVVVKYKDNASASAVKSARAK
               MKKRVSLIASFVLMASAALPSAIFAEEVDSQAGKLYAPGQVVVKYKDNASASAVKSARAK
Sbjct10        MKKRVSLIASFVLMASAALPSAIFAEEVDSQAGKLYAPGQVVVKYKDNASASAVKSARAK Query   61     ANGTVMEKNNKLGFEVVKVKGSVEATIEKLKKDPNVEYAEPNYYLHATYTPNDPYFSSRQ
               ANGTVMEKNNKLGFEVVKVKGSVEATIEKLKKDPNVEYAEPNYYLHA+YTPNDPYFS+RQ
Sbjct   61     ANGTVMEKNNKLGFEVVKVKGSVEATIEKLKKDPNVEYAEPNYYLHASYTPNDPYFSTRQ  120

Query   121    YGPQKIQAPQAWDIAEGSGVKIAIVDTGVQSNHPDLAGKVVGGWDFVDNDSTPQDGNGHG
               YGPQKIQAPQAWDI EGSG KIAIVDTGVQSNHPDLAGKVVGGWDFVDNDSTPQDGNGHG
Sbjct   121    YGPQKIQAPQAWDITEGSGAKIAIVDTGVQSNHPDLAGKVVGGWDFVDNDSTPQDGNGHG  180

Query   181    THCAGIAAAVTNNSTGIAGTAPKASILAVRVLDNSGSGTWTAVANGITYAADQGAKVISL
               THCAGIAAAVTNNSTGIAGTAPKASILAVRVLDNSGSGTWTAVANGITYAADQGA VISL
Sbjct   181    THCAGIAAAVTNNSTGIAGTAPKASILAVRVLDNSGSGTWTAVANGITYAADQGADVISL  240

Query   241    SLGGTVGNSGLQQAVDYAWNKGSVVVAAAGNAGNTAPNYPAYYSNAIAVASTDQNDNKSS
               SLGGTVGNSGLQQAV+YAWNKGSVVVAAAGNAGNTAP+YPAYYSNAIAVASTDQNDNKSS
Sbjct   241    SLGGTVGNSGLQQAVNYAWNKGSVVVAAAGNAGNTAPHYPAYYSNAIAVASTDQNDNKSS  300

Query   301    FSTYGSWVDVAAPGSSIYSTYPTSTYASLSGTSMATPHVAGVAGLLASQGRSASNIRAAI
               FSTYGSWVDVAAPGSSIY+TYPTSTYASLSGTSMATPHVAGVAGLLASQGRSASNIRAAI
Sbjct   301    FSTYGSWVDVAAPGSSIYATYPTSTYASLSGTSMATPHVAGVAGLLASQGRSASNIRAAI  360

Query   361    ENTADKISGTGTYWAKGRVNAYKAVQY
               ENTADKISGTG+YWAKGRVNAYKAVQY
Sbjct   361    ENTADKISGTGSYWAKGRVNAYKAVQY
```

Figure 12

*No 16 (Query; SEQ ID NO: 2) v's thermitase precursor [Laceyella sacchari] (Subject; SEQ ID NO: 20)*

```
Score        Expect    Method                Identities     Positives     Gaps
768 bits(1984) 0.0     Compositional matrix  384/387(99%)   386/387(99%)  0/387(0%)
Query   1    MKKRVSLIASFVLNASAALPSAIFAEEVDSQAGKLYAPGQVVVKYKDNASASAVKSARAK
             MKKRVSLIASFVL ASAALPSAIFAEEVDSQAGKLYAPGQVVVKYKDNASASAVKSARAK
Sbjct  16    MKKRVSLIASFVLMASAALPSAIFAEEVDSQAGKLYAPGQVVVKYKDNASASAVKSARAK Query  61    ANGTVMEKNNKLGFEVVKVKGSVEATIEKLKKDPNVEYAEPNYYLHATYTPNDPYFSSRQ
             ANGTVMEKNNKLGFEVVKVKGSVEATIEKLKKDPNVEYAEPNYYLHATYTPNDPYFSSRQ
Sbjct  61    ANGTVMEKNNKLGFEVVKVKGSVEATIEKLKKDPNVEYAEPNYYLHATYTPNDPYFSSRQ   120
Query 121    YGPQKIQAPQAWDIAEGSGVKIAIVDTGVQSNHPDLAGKVVGGWDFVDNDSTPQDGNGHG
             YGPQKIQAPQAWDIAEGSGVKIAIVDTGVQSNHPDLAGKVVGGWDFVDNDSTPQDGNGHG
Sbjct 121    YGPQKIQAPQAWDIAEGSGVKIAIVDTGVQSNHPDLAGKVVGGWDFVDNDSTPQDGNGHG   180
Query 181    THCAGIAAAVTNNSTGIAGTAPKASILAVRVLNNSGSGTWTAVANGITYAADQGAKVISL
             THCAGIAAAVTNNSTGIAGTAPKASILAVRVL+NSGSGTWTAVANGITYAADQGAKVISL
Sbjct 181    THCAGIAAAVTNNSTGIAGTAPKASILAVRVLDNSGSGTWTAVANGITYAADQGAKVISL   240
Query 241    SLGGTVGNSGLQQAVDYAWSKGSVVVAAAGNAGNTAPNYPAYYSNAIAVASTDQNDNKSS
             SLGGTVGNSGLQQAVDYAW+KGSVVVAAAGNAGNTAPNYPAYYSNAIAVASTDQNDNKSS
Sbjct 241    SLGGTVGNSGLQQAVDYAWNKGSVVVAAAGNAGNTAPNYPAYYSNAIAVASTDQNDNKSS Query 301    FSTYGSWVDVAAPGSSIYSTYPTSTYASLSGTSMATPHVAGVAGLLASQGRSASNIRAAI
             FSTYGSWVDVAAPGSSIYSTYPTSTYASLSGTSMATPHVAGVAGLLASQGRSASNIRAAI
Sbjct 301    FSTYGSWVDVAAPGSSIYSTYPTSTYASLSGTSMATPHVAGVAGLLASQGRSASNIRAAI Query 361    ENTADKISGTGTYWAKGRVNAYKAVQY   387
             ENTADKISGTGTYWAKGRVNAYKAVQY
Sbjct 361    ENTADKISGTGTYWAKGRVNAYKAVQY   387
```

Figure 13

*No 10 (Query; SEQ ID NO: 5) v's thermitase precursor [Laceyella sacchari] (Subject; SEQ ID NO: 20)*

```
Score        Expect    Method                Identities     Positives     Gaps
754 bits(1946) 0.0     Compositional matrix  375/387(97%)   383/387(98%)  0/387(0%)
Query   1    MKKRVSLIASFVLNASAALPSAIFAEEVDSQAGKLYAPGQVVVKYKDNASASAVKSARAK
             MKKRVSLIASFVL ASAALPSAIFAEEVDSQAGKLYAPGQVVVKYKDNASASAVKSARAK
Sbjct   1    MKKRVSLIASFVLMASAALPSAIFAEEVDSQAGKLYAPGQVVVKYKDNASASAVKSARAK   60
Query  61    ANGTVMEKNNKLGFEVVKVKGSVEATIEKLKKDPNVEYAEPNYYLHATYTPNDPYFSSRQ
             ANGTVMEKNNKLGFEVVKVKGSVEATIEKLKKDPNVEYAEPNYYLHA+YTPNDPYFS+RQ
Sbjct  61    ANGTVMEKNNKLGFEVVKVKGSVEATIEKLKKDPNVEYAEPNYYLHASYTPNDPYFSTRQ   120
Query 121    YGPQKIQAPQAWDIAEGSGVKIAIVDTGVQSNHPDLAGKVVGGWDFVDNDSTPQDGNGHG
             YGPQKIQAPQAWDI EGSG KIAIVDTGVQSNHPDLAGKVVGGWDFVDNDSTPQDGNGHG
Sbjct 121    YGPQKIQAPQAWDITEGSGAKIAIVDTGVQSNHPDLAGKVVGGWDFVDNDSTPQDGNGHG Query 181    THCAGIAAAVTNNSTGIAGTAPKASILAVRVLNNSGSGTWTAVANGITYAADQGAKVISL
             THCAGIAAAVTNNSTGIAGTAPKASILAVRVL+NSGSGTWTAVANGITYAADQGA VISL
Sbjct 181    THCAGIAAAVTNNSTGIAGTAPKASILAVRVLDNSGSGTWTAVANGITYAADQGADVISL   240
Query 241    SLGGTVGNSGLQQAVDYAWSKGSVVVAAAGNAGNTAPNYPAYYSNAIAVASTDQNDNKSS
             SLGGTVGNSGLQQAV+YAW+KGSVVVAAAGNAGNTAP YPAYYSNAIAVASTDQNDNKSS
Sbjct 241    SLGGTVGNSGLQQAVNYAWNKGSVVVAAAGNAGNTAPHYPAYYSNAIAVASTDQNDNKSS   300
Query 301    FSTYGSWVDVAAPGSSIYSTYPTSTYASLSGTSMATPHVAGVAGLLASQGRSASNIRAAI
             FSTYGSWVDVAAPGSSIY+TYPTSTYASLSGTSMATPHVAGVAGLLASQGRSASNIRAAI
Sbjct 301    FSTYGSWVDVAAPGSSIYATYPTSTYASLSGTSMATPHVAGVAGLLASQGRSASNIRAAI   360
Query 361    ENTADKISGTGTYWAKGRVNAYKAVQY   387
             ENTADKISGTG+YWAKGRVNAYKAVQY
Sbjct 361    ENTADKISGTGSYWAKGRVNAYKAVQY   387
```

Figure 14

*No 16 (Query; SEQ ID NO: 3) v's 10 (Subject; SEQ ID NO: 17); gene mature*

```
    Score       Expect   Identities     Gaps      Strand
1319 bits(714)  0.0      798/840(95%)   0/840(0%) Plus/Plus Query  1    TACACACCTAACGATCCTTACTTCAGCTCCCGCCAATACGGCCCACAAAAAATCCAAGCG
            |||||  ||||||||||||||||||||| ||||||||||||||||||||||||||||||
Sbjct  1    TACACGCCTAACGATCCTTACTTCAGCACCCGCCAATACGGCCCACAAAAAATCCAAGCG Query  61   CCGCAGGCATGGGACATCGCTGAAGGCTCCGGCGTGAAAATCGCCATCGTCGACACCGGG
            ||  || ||||||||||| |||||||||||||| |  |||||||||||||||||||||
Sbjct  61   CCACAAGCATGGGACATCACTGAAGGCTCCGGCGCGAAGATCGCCATCGTCGACACCGGG Query  121  GTGCAATCCAACCATCCCGACTTGGCCGGTAAAGTAGTGGGCGGTTGGGACTTCGTTGAC
            || ||||||||||||||||||||||||||||||||||||||||||||||||||||||||
Sbjct  121  GTACAATCCAACCATCCCGACTTGGCCGGTAAAGTAGTGGGCGGTTGGGACTTCGTTGAC Query  181  AACGACTCCACTCCGCAAGATGGCAACGGCCACGGTACACACTGCGCTGGTATCGCCGCA
            ||||||||| || |||||||||||||||||||||||||| |||||||||||||||||||
Sbjct  181  AACGACTCCACGCCACAAGATGGCAACGGCCACGGTACCCACTGCGCTGGTATCGCCGCA Query  241  GCAGTGACCAACAACAGCACCGGGATCGCTGGTACTGCCCCGAAAGCGTCAATCCTCGCT
            |||||||||||||||||||||||||||||||||||||| || ||||||||| ||||||||
Sbjct  241  GCAGTGACCAACAACAGCACCGGGATCGCTGGTACTGCTCCAAAAGCGTCGATCCTCGCT Query  301  GTGCGCGTGCTGGACAACAGCGGTAGCGGCACCTGGACTGCTGTCGCCAACGGTATCACC
            |||||||||||||||||||| |||||||||||||||||||||||||||||||||||||||
Sbjct  301  GTGCGCGTGCTGGACAACAGTGGTAGCGGCACCTGGACTGCTGTCGCCAACGGTATCACC Query  361  TATGCTGCAGACCAAGGCGCTAAAGTCATCAGCTTGAGCTTGGGCGGCACCGTTGGTAAC
            ||||| ||||||||||| |||| ||||||||||||||||||||||||||||||  |||||
Sbjct  361  TATGCCGCAGACCAAGGTGCTGACGTCATCAGCTTGAGCTTGGGCGGCACCGTCGGTAAC Query  421  TCCGGTCTGCAACAAGCTGTCGACTACGCTTGGAACAAAGGTTCCGTTGTCGTGGCCGCG
            |||||||||||||||||||||| ||||||||||||||||||| ||||||||||||||||
Sbjct  421  TCCGGTCTGCAACAAGCTGTCAACTACGCTTGGAACAAAGGTTCTGTTGTCGTGGCCGCA Query  481  GCTGGTAACGCCGGCAACACCGCTCCTAACTATCCCGCTTACTATTCCAACGCCATCGCG
            |||||||||||||||||||||||||| |||||| ||  ||| |||||||||||||||||
Sbjct  481  GCTGGTAACGCCGGCAACACCGCTCCTCACTATCCTGCATACTATTCCAACGCCATCGCG Query  541  GTAGCTTCTACTGACCAAAATGACAACAAATCCTCCTTCTCCACTTACGGTTCCTGGGTA
            ||||||||||||||||||||||||||||||||||||||||||||||||||||||||||||
Sbjct  541  GTAGCTTCTACTGACCAAAATGACAACAAATCCTCCTTCTCCACTTACGGTTCCTGGGTA Query  601  GATGTAGCTGCTCCTGGTTCCAGCATCTATTCCACCTACCCGACCAGCACCTACGCTTCC
            ||||||||  |||||||||||||||||| | || || ||||||||||||||||||||||
Sbjct  601  GATGTAGCCGCTCCTGGTTCCAGCATCTATGCTACTTATCCGACCAGCACCTACGCTTCC Query  661  TTGAGCGGTACCTCCATGGCTACTCCTCACGTAGCTGGTGTGGCTGGACTCTTGGCTTCC
            ||||||||||||||||||||||||| || |||| ||||||| ||||||||| ||||||||
Sbjct  661  TTGAGCGGTACCTCCATGGCTACTCCCCATGTGGCTGGAGTGGCTGGACTCCTGGCTTCC Query  721  CAAGGCCGTAGCGCTTCCAATATCCGCGCCGCCATTGAAAACACCGCCGACAAAATCAGC
            ||||||||||| ||||||| ||||||||||||| ||||||||||||||||||||||||||
Sbjct  721  CAAGGCCGTAGTGCTTCCAACATCCGCGCCGCTATTGAAAACACCGCCGACAAAATCAGC Query  781  GGCACTGGCACCTACTGGGCCAAAGGACGCGTCAACGCTTACAAAGCTGTTCAGTACTAA
            ||||| ||| |||||||||||||||| ||||||||||||||||||||||||||||||||
Sbjct  781  GGCACCGGCTCCTACTGGGCCAAAGGGCGCGTCAACGCTTACAAAGCTGTTCAGTACTAA
```

Figure 15

*No 16 (Query; SEQ ID NO: 22) v's 10 (Subject; SEQ ID NO: 6)*

```
   Score      Expect    Identities        Gaps      Strand
1862 bits(1008) 0.0    1112/1164(96%)  0/1164(0%) Plus/Plus Query    1    ATGAAGAAACGCGTTTCCCTCATCGCTTCCTTCGTTTTGATGGCAAGCGCCGCCCTGCCT
              ||||||||||||||||||||||||||||||||||||||||||| ||||||||||||||||
Sbjct    1    ATGAAGAAACGCGTTTCCCTCATCGCTTCCTTCGTTTTGATGGCCAGCGCCGCCCTGCCT Query   61    TCCGCCATTTTCGCTGAGGAAGTAGATAGCCAAGCGGGTAAACTCTATGCTCCAGGGCAA
              ||||||||||||||| |||||||||||||||||||||||||||||||| || || ||||||
Sbjct   61    TCCGCCATTTTCGCAGAGGAAGTAGATAGCCAAGCGGGTAAACTCTACGCCCCCGGGCAA Query  121    GTCGTGGTGAAATACAAAGACAATGCTTCGGCCAGCGCCGTCAAATCTGCCCGCGCCAAA
              || ||||||||||||||||||||||||||||||||||| ||||||||||||||||||||||
Sbjct  121    GTTGTGGTGAAATACAAAGACAATGCTTCGGCCAGCGCTGTCAAATCTGCCCGCGCCAAA Query  181    GCCAACGGTACAGTCATGGAGAAAAACAACAAGCTCGGCTTTGAAGTGGTCAAAGTGAAA
              ||||||||||||||||||||||||||||||||||||||| ||||||||||||||||||||
Sbjct  181    GCCAACGGTACAGTCATGGAGAAAAACAACAAGCTCGGCTTCGAAGTGGTCAAAGTGAAA Query  241    GGCTCTGTGGAAGCGACCATCGAAAAGCTGAAAAAAGACCCCAACGTGGAATATGCTGAA
              |||||||||||||||||||||||||||||||||||||||||||||||||||||||||||
Sbjct  241    GGCTCTGTGGAAGCGACCATCGAAAAGCTGAAAAAAGACCCCAACGTGGAATATGCTGAG Query  301    CCCAACTACTATCTCCACGCTACCTACACACCTAACGATCCTTACTTCAGCTCCCGCCAA
              ||||||||||||||||||||||| ||||||| |||||||||||||||||||| |||||||
Sbjct  301    CCCAACTACTATCTCCACGCTTCCTACACGCCTAACGATCCTTACTTCAGCACCCGCCAA Query  361    TACGGCCCACAAAAAATCCAAGCGCCGCAGGCATGGGACATCGCTGAAGGCTCCGGCGTG
              ||||||||||||||||||||||||||| || |||||||||||| ||||||||||||||| |
Sbjct  361    TACGGCCCACAAAAAATCCAAGCGCCACAAGCATGGGACATCACTGAAGGCTCCGGCGCG Query  421    AAAATCGCCATCGTCGACACCGGGGTGCAATCCAACCATCCCGACTTGGCCGGTAAAGTA
              || |||||||||||||||||||||| |||||||||||||||||||||||||||||||||
Sbjct  421    AAGATCGCCATCGTCGACACCGGGGTACAATCCAACCATCCCGACTTGGCCGGTAAAGTA Query  481    GTGGGCGGTTGGGACTTCGTTGACAACGACTCCACTCCGCAAGATGGCAACGGCCACGGT
              |||||||||||||||||||||||||||||||||| ||||||||||||||||||||||||
Sbjct  481    GTGGGCGGTTGGGACTTCGTTGACAACGACTCCACGCCACAAGATGGCAACGGCCACGGT Query  541    ACACACTGCGCTGGTATCGCCGCAGCAGTGACCAACAACAGCACCGGGATCGCTGGTACT
              || |||||||||||||||||||||||||||||||||||||||||||||||||||||||||
Sbjct  541    ACCCACTGCGCTGGTATCGCCGCAGCAGTGACCAACAACAGCACCGGGATCGCTGGTACT Query  601    GCCCCGAAAGCGTCAATCCTCGCTGTGCGCGTGCTGGACAACAGCGGTAGCGGCACCTGG
              || || ||||||||| ||||||||||||||||||||||||||||| ||||||||||||||
Sbjct  601    GCTCCAAAAGCGTCGATCCTCGCTGTGCGCGTGCTGGACAACAGTGGTAGCGGCACCTGG Query  661    ACTGCTGTCGCCAACGGTATCACCTATGCTGCAGACCAAGGCGCTAAAGTCATCAGCTTG
              ||||||||||||||||||||||||||||| |||||||||| ||||| ||| | |||||||||
Sbjct  661    ACTGCTGTCGCCAACGGTATCACCTATGCCGCAGACCAAGGTGCTGACGTCATCAGCTTG Query  721    AGCTTGGGCGGCACCGTTGGTAACTCCGGTCTGCAACAAGCTGTCGACTACGCTTGGAAC
              ||||||||||||||||| |||||||||||||||||||||||||||| |||||||||||||
Sbjct  721    AGCTTGGGCGGCACCGTCGGTAACTCCGGTCTGCAACAAGCTGTCAACTACGCTTGGAAC
```

*Figure continues on next sheet.*

Figure 15, continued.

```
Query  781   AAAGGTTCCGTTGTCGTGGCCGCGGCTGGTAACGCCGGCAACACCGCTCCTAACTATCCC
             ||||||| ||||||||||||||| ||||||||||||||||||||||||||| |||||||
Sbjct  781   AAAGGTTCTGTTGTCGTGGCCGCAGCTGGTAACGCCGGCAACACCGCTCCTCACTATCCT Query  841   GCTTACTATTCCAACGCCATCGCGGTAGCTTCTACTGACCAAAATGACAACAAATCCTCC
             || |||||||||||||||||||||||||||||||||||||||||||||||||||||||||
Sbjct  841   GCATACTATTCCAACGCCATCGCGGTAGCTTCTACTGACCAAAATGACAACAAATCCTCC Query  901   TTCTCCACTTACGGTTCCTGGGTAGATGTAGCTGCTCCTGGTTCCAGCATCTATTCCACC
             |||||||||||||||||||||||||||||||| |||||||||||||||||||| | ||
Sbjct  901   TTCTCCACTTACGGTTCCTGGGTAGATGTAGCCGCTCCTGGTTCCAGCATCTATGCTACT Query  961   TACCCGACCAGCACCTACGCTTCCTTGAGCGGTACCTCCATGGCTACTCCTCACGTAGCT
             || |||||||||||||||||||||||||||||||||||||||||||||||| || || |||
Sbjct  961   TATCCGACCAGCACCTACGCTTCCTTGAGCGGTACCTCCATGGCTACTCCCCATGTGGCT Query  1021  GGTGTGGCTGGACTCTTGGCTTCCCAAGGCCGTAGCGCTTCCAATATCCGCGCCGCCATT
             || ||||||||||||| |||||||||||||||||| |||||||| |||||||||||| |||
Sbjct  1021  GGAGTGGCTGGACTCCTGGCTTCCCAAGGCCGTAGTGCTTCCAACATCCGCGCCGCTATT Query  1081  GAAAACACCGCCGACAAAATCAGCGGCACTGGCACCTACTGGGCCAAAGGACGCGTCAAC
             ||||||||||||||||||||||||||||||| ||| |||||||||||||||| ||||||||
Sbjct  1081  GAAAACACCGCCGACAAAATCAGCGGCACCGGCTCCTACTGGGCCAAAGGGCGCGTCAAC Query  1141  GCTTACAAAGCTGTTCAGTACTAA
             ||||||||||||||||||||||||
Sbjct  1141  GCTTACAAAGCTGTTCAGTACTAA
```

Figure 16

*No 16 (Subject, SEQ ID NO: 3) v's thermitase precursor [Laceyella sacchari] (Query; SEQ ID: 21)*

```
   Score      Expect    Identities      Gaps        Strand
2073 bits(1122) 0.0    1150/1164(99%)  0/1164(0%)  Plus/Plus Query    1    ATGAAGAAACGCGTTTCCCTCATCGCTTCCTTCGTTTTGAATGCAAGCGCCGCTCTTCCT
              |||||||||||||||||||||||||||||||||||||||| |||||||||| || |||
Sbjct    1    ATGAAGAAACGCGTTTCCCTCATCGCTTCCTTCGTTTTGATGGCAAGCGCCGCCCTGCCT Query   61    TCCGCCATTTTCGCTGAGGAAGTAGATAGCCAAGCGGGTAAACTCTATGCTCCAGGGCAA
              ||||||||||||||||||||||||||||||||||||||||||||||||||||||||||||
Sbjct   61    TCCGCCATTTTCGCTGAGGAAGTAGATAGCCAAGCGGGTAAACTCTATGCTCCAGGGCAA Query  121    GTCGTGGTGAAATACAAAGACAATGCTTCGGCCAGCGCCGTCAAATCTGCCCGCGCCAAA
              ||||||||||||||||||||||||||||||||||||||||||||||||||||||||||||
Sbjct  121    GTCGTGGTGAAATACAAAGACAATGCTTCGGCCAGCGCCGTCAAATCTGCCCGCGCCAAA Query  181    GCCAACGGTACAGTCATGG      CAACAAGCTCGGCTTTGAAGTGGTCAAAGTGAAA
              ||||||||||||||||||| ||||||||||||||||||||||||||||||||||
Sbjct  181    GCCAACGGTACAGTCATGGAGAAAAACAACAAGCTCGGCTTTGAAGTGGTCAAAGTGAAA Query  241    GGCTCTGTGGAAGCGACCATCGAAAAGCTGAAAAAAGACCCCAACGTGGAATATGCTGAA
              ||||||||||||||||||||||||||||||||||||||||||||||||||||||||||||
Sbjct  241    GGCTCTGTGGAAGCGACCATCGAAAAGCTGAAAAAAGACCCCAACGTGGAATATGCTGAA Query  301    CCCAACTACTATCTCCACGCTACCTACACACCTAACGATCCTTACTTCAGCTCCCGCCAA
              ||||||||||||||||||||||||||||||||||||||||||||||||||||||||||||
Sbjct  301    CCCAACTACTATCTCCACGCTACCTACACACCTAACGATCCTTACTTCAGCTCCCGCCAA Query  361    TACGGCCCACAAAAAATCCAAGCGCCGCAAGCATGGGACATCGCTGAAGGCTCCGGCGTG
              ||||||||||||||||||||||||||||||| ||||||||||||||||||||||||||||
Sbjct  361    TACGGCCCACAAAAAATCCAAGCGCCGCAGGCATGGGACATCGCTGAAGGCTCCGGCGTG Query  421    AAAATCGCCATCGTCGACACCGGGGTGCAATCCAACCATCCCGACTTGGCCGGTAAAGTA
              ||||||||||||||||||||||||||||||||||||||||||||||||||||||||||||
Sbjct  421    AAAATCGCCATCGTCGACACCGGGGTGCAATCCAACCATCCCGACTTGGCCGGTAAAGTA Query  481    GTGGGCGGTTGGGACTTCGTTGACAACGACTCCACTCCGCAAGATGGCAACGGCCACGGT
              ||||||||||||||||||||||||||||||||||||||||||||||||||||||||||||
Sbjct  481    GTGGGCGGTTGGGACTTCGTTGACAACGACTCCACTCCGCAAGATGGCAACGGCCACGGT Query  541    ACACACTGCGCTGGTATCGCCGCAGCAGTGACCAACAACAGCACCGGGATCGCTGGTACT
              ||||||||||||||||||||||||||||||||||||||||||||||||||||||||||||
Sbjct  541    ACACACTGCGCTGGTATCGCCGCAGCAGTGACCAACAACAGCACCGGGATCGCTGGTACT Query  601    GCTCCGAAAGCATCGATCCTCGCTGTGCGCGTGCTGAACAACAGCGGTAGCGGCACCTGG
              || |||||||| || ||||||||||||||||||||| |||||||||||||||||||||||
Sbjct  601    GCCCCGAAAGCGTCAATCCTCGCTGTGCGCGTGCTGGACAACAGCGGTAGCGGCACCTGG Query  661    ACTGCTGTCGCCAACGGTATCACCTATGCTGCAGACCAAGGCGCTAAAGTCATCAGCTTG
              ||||||||||||||||||||||||||||||||||||||||||||||||||||||||||||
Sbjct  661    ACTGCTGTCGCCAACGGTATCACCTATGCTGCAGACCAAGGCGCTAAAGTCATCAGCTTG Query  721    AGCTTGGGCGGCACCGTTGGTAACTCCGGTCTGCAACAAGCTGTCGACTACGCTTGGAGC
              |||||||||||||||||||||||||||||||||||||||||||||||||||||||||| |
Sbjct  721    AGCTTGGGCGGCACCGTTGGTAACTCCGGTCTGCAACAAGCTGTCGACTACGCTTGGAAC
```

*Figure continues on next sheet.*

Figure 16, continued.

```
Query  781   AAAGGTTCCGTTGTCGTGGCCGCGGCTGGTAACGCCGGCAACACCGCTCCTAACTATCCC
             ||||||||||||||||||||||||||||||||||||||||||||||||||||||||||||
Sbjct  781   AAAGGTTCCGTTGTCGTGGCCGCGGCTGGTAACGCCGGCAACACCGCTCCTAACTATCCC Query  841   GCTTACTATTCCAACGCCATCGCGGTAGCTTCCACTGACCAAAACGACAACAAATCCTCC
             |||||||||||||||||||||||||||||||||| ||||||||||| |||||||||||||
Sbjct  841   GCTTACTATTCCAACGCCATCGCGGTAGCTTCTACTGACCAAAATGACAACAAATCCTCC Query  901   TTCTCCACTTACGGTTCCTGGGTAGATGTAGCTGCTCCTGGTTCCAGCATCTATTCCACC
             ||||||||||||||||||||||||||||||||||||||||||||||||||||||||||||
Sbjct  901   TTCTCCACTTACGGTTCCTGGGTAGATGTAGCTGCTCCTGGTTCCAGCATCTATTCCACC Query  961   TACCCGACCAGCACCTACGCTTCCTTGAGCGGTACCTCCATGGCTACTCCTCACGTAGCT
             ||||||||||||||||||||||||||||||||||||||||||||||||||||||||||||
Sbjct  961   TACCCGACCAGCACCTACGCTTCCTTGAGCGGTACCTCCATGGCTACTCCTCACGTAGCT Query  1021  GGTGTGGCTGGACTCTTGGCTTCCCAAGGCCGTAGCGCTTCCAATATCCGCGCCGCCATT
             ||||||||||||||||||||||||||||||||||||||||||||||||||||||||||||
Sbjct  1021  GGTGTGGCTGGACTCTTGGCTTCCCAAGGCCGTAGCGCTTCCAATATCCGCGCCGCCATT Query  1081  GAAAACACCGCCGACAAAATCAGCGGCACTGGCACCTACTGGGCCAAAGGGCGCGTCAAC
             |||||||||||||||||||||||||||||||||||||||||||||||||||| |||||||
Sbjct  1081  GAAAACACCGCCGACAAAATCAGCGGCACTGGCACCTACTGGGCCAAAGGACGCGTCAAC Query  1141  GCTTACAAAGCTGTTCAGTACTAA
             ||||||||||||||||||||||||
Sbjct  1141  GCTTACAAAGCTGTTCAGTACTAA
```

Figure 17

*No 10 (SEQ ID NO: 6) (subject) v's thermitase precursor [Laceyella sacchari] (Query; SEQ ID: 21)*

```
  Score      Expect    Identities      Gaps       Strand
1829 bits(990) 0.0     1106/1164(95%)  0/1164(0%) Plus/Plus Query  1    ATGAAGAAACGCGTTTCCCTCATCGCTTCCTTCGTTTTGAATGCAAGCGCCGCTCTTCCT
            |||||||||||||||||||||||||||||||||||||||||| || |||||||| || |||
Sbjct  1    ATGAAGAAACGCGTTTCCCTCATCGCTTCCTTCGTTTTGATGGCCAGCGCCGCCCTGCCT Query  61   TCCGCCATTTTCGCTGAGGAAGTAGATAGCCAAGCGGGTAAACTCTATGCTCCAGGGCAA
            |||||||||||||| ||||||||||||||||||||||||||||||||| || || ||||||
Sbjct  61   TCCGCCATTTTCGCAGAGGAAGTAGATAGCCAAGCGGGTAAACTCTACGCCCCCGGGCAA Query  121  GTCGTGGTGAAATACAAAGACAATGCTTCGGCCAGCGCCGTCAAATCTGCCCGCGCCAAA
            || |||||||||||||||||||||||||||||||||| ||||||||||||||||||||||
Sbjct  121  GTTGTGGTGAAATACAAAGACAATGCTTCGGCCAGCGCTGTCAAATCTGCCCGCGCCAAA Query  181  GCCAACGGTACAGTCATGG      CAACAAGCTCGGCTTTGAAGTGGTCAAAGTGAAA
            |||||||||||||||||||      |||||||||||||| |||||||||||||||||||
Sbjct  181  GCCAACGGTACAGTCATGGAGAAAAACAACAAGCTCGGCTTCGAAGTGGTCAAAGTGAAA Query  241  GGCTCTGTGGAAGCGACCATCGAAAAGCTGAAAAAAGACCCCAACGTGGAATATGCTGAA
            ||||||||||||||||||||||||||||||||||||||||||||||||||||||||||| 
Sbjct  241  GGCTCTGTGGAAGCGACCATCGAAAAGCTGAAAAAAGACCCCAACGTGGAATATGCTGAG Query  301  CCCAACTACTATCTCCACGCTACCTACACACCTAACGATCCTTACTTCAGCTCCCGCCAA
            |||||||||||||||||||||| ||||||| ||||||||||||||||||||| |||||||
Sbjct  301  CCCAACTACTATCTCCACGCTTCCTACACGCCTAACGATCCTTACTTCAGCACCCGCCAA Query  361  TACGGCCCACAAAAAATCCAAGCGCCGCAAGCATGGGACATCGCTGAAGGCTCCGGCGTG
            |||||||||||||||||||||||||| ||||||||||||||| |||||||||||||||| |
Sbjct  361  TACGGCCCACAAAAAATCCAAGCGCCACAAGCATGGGACATCACTGAAGGCTCCGGCGCG Query  421  AAAATCGCCATCGTCGACACCGGGGTGCAATCCAACCATCCCGACTTGGCCGGTAAAGTA
            || |||||||||||||||||||||| |||||||||||||||||||||||||||||||||
Sbjct  421  AAGATCGCCATCGTCGACACCGGGGTACAATCCAACCATCCCGACTTGGCCGGTAAAGTA Query  481  GTGGGCGGTTGGGACTTCGTTGACAACGACTCCACTCCGCAAGATGGCAACGGCCACGGT
            ||||||||||||||||||||||||||||||||| || |||||||||||||||||||||||
Sbjct  481  GTGGGCGGTTGGGACTTCGTTGACAACGACTCCACGCCACAAGATGGCAACGGCCACGGT Query  541  ACACACTGCGCTGGTATCGCCGCAGCAGTGACCAACAACAGCACCGGGATCGCTGGTACT
            || ||||||||||||||||||||||||||||||||||||||||||||||||||||||||||
Sbjct  541  ACCCACTGCGCTGGTATCGCCGCAGCAGTGACCAACAACAGCACCGGGATCGCTGGTACT Query  601  GCTCCGAAAGCATCGATCCTCGCTGTGCGCGTGCTGAACAACAGCGGTAGCGGCACCTGG
            ||||| ||||| |||||||||||||||||||||||| |||||| ||||||||||||||||
Sbjct  601  GCTCCAAAAGCGTCGATCCTCGCTGTGCGCGTGCTGGACAACAGTGGTAGCGGCACCTGG Query  661  ACTGCTGTCGCCAACGGTATCACCTATGCTGCAGACCAAGGCGCTAAAGTCATCAGCTTG
            |||||||||||||||||||||||||||||| |||||||||||| ||| | |||||||||||
Sbjct  661  ACTGCTGTCGCCAACGGTATCACCTATGCCGCAGACCAAGGTGCTGACGTCATCAGCTTG Query  721  AGCTTGGGCGGCACCGTTGGTAACTCCGGTCTGCAACAAGCTGTCGACTACGCTTGGAGC
            ||||||||||||||||| |||||||||||||||||||||||||||| ||||||||||| |
Sbjct  721  AGCTTGGGCGGCACCGTCGGTAACTCCGGTCTGCAACAAGCTGTCAACTACGCTTGGAAC
```

*Figure continues on next sheet.*

Figure 17, continued.

```
Query  781   AAAGGTTCCGTTGTCGTGGCCGCGGCTGGTAACGCCGGCAACACCGCTCCTAACTATCCC
             ||||||||  |||||||||||||| |||||||||||||||||||||||||||| |||||||
Sbjct  781   AAAGGTTCTGTTGTCGTGGCCGCAGCTGGTAACGCCGGCAACACCGCTCCTCACTATCCT Query  841   GCTTACTATTCCAACGCCATCGCGGTAGCTTCCACTGACCAAAACGACAACAAATCCTCC
             || ||||||||||||||||||||||||||| || ||||||||||| ||||||||||||||
Sbjct  841   GCATACTATTCCAACGCCATCGCGGTAGCTTCTACTGACCAAAATGACAACAAATCCTCC Query  901   TTCTCCACTTACGGTTCCTGGGTAGATGTAGCTGCTCCTGGTTCCAGCATCTATTCCACC
             ||||||||||||||||||||||||||||||||| |||||||||||||||||||| | ||
Sbjct  901   TTCTCCACTTACGGTTCCTGGGTAGATGTAGCCGCTCCTGGTTCCAGCATCTATGCTACT Query  961   TACCCGACCAGCACCTACGCTTCCTTGAGCGGTACCTCCATGGCTACTCCTCACGTAGCT
             || ||||||||||||||||||||||||||||||||||||||||||||||| ||  | |||
Sbjct  961   TATCCGACCAGCACCTACGCTTCCTTGAGCGGTACCTCCATGGCTACTCCCCATGTGGCT Query  1021  GGTGTGGCTGGACTCTTGGCTTCCCAAGGCCGTAGCGCTTCCAATATCCGCGCCGCCATT
             || |||||||||||| |||||||||||||||||||| |||||||| |||||||||| |||
Sbjct  1021  GGAGTGGCTGGACTCCTGGCTTCCCAAGGCCGTAGTGCTTCCAACATCCGCGCCGCTATT Query  1081  GAAAACACCGCCGACAAAATCAGCGGCACTGGCACCTACTGGGCCAAAGGGCGCGTCAAC
             |||||||||||||||||||||||||||||| ||| |||||||||||||||||||||||||
Sbjct  1081  GAAAACACCGCCGACAAAATCAGCGGCACCGGCTCCTACTGGGCCAAAGGGCGCGTCAAC Query  1141  GCTTACAAAGCTGTTCAGTACTAA
             ||||||||||||||||||||||||
Sbjct  1141  GCTTACAAAGCTGTTCAGTACTAA
```

COMPOSITION AND USES THEREOF

CROSS-REFERENCE TO RELATED APPLICATIONS

This application is the 35 U.S.C. § 371 national stage application of PCT Application No. PCT/EP2016/082557, filed Dec. 23, 2016, where the PCT claims priority to GB. Patent Application Serial No. 1522814.1, titled "COMPOSITION AND USES THEREOF" filed on Dec. 23, 2015, both of which are herein incorporated by reference in their entireties.

REFERENCE TO SEQUENCE LISTING

The Sequence Listing submitted Feb. 12, 2022, as a text file named "2022-02-12_Substitute_Sequence_Listing_AYL-00001-U-US-01_ST25.txt" created on Feb. 11, 2022, and having a size of 27,750 bytes is hereby incorporated by reference.

TECHNICAL FIELD OF THE INVENTION

The invention relates to novel proteases for degrading proteinaceous infectious agents (prions).

BACKGROUND TO THE INVENTION

Transmissible Spongiform Encephalopathies (TSEs) or prion diseases are fatal neurodegenerative disorders with the ability to affect both animals and humans and include scrapie, Bovine Spongiform Encephalopathy (BSE) and chronic wasting disease (CWD) in animals and Creutzfeldt-Jakob disease (CJD), Gerstmann-Sträussler-Scheinker syndrome and Fatal Familial Insomnia in humans. These disorders, which are generally associated with the accumulation in the brain of an abnormal partially protease resistant isoform ($PrP^{Sc}$) of the normal endogenous prion protein ($PrP^C$), can be infectious, genetic or sporadic in origin.

There is continuing concern over the potential to transmit prion diseases in the hospital sector through the use of contaminated instruments. These disorders are generally associated with the accumulation in the brain of an abnormal partially protease resistant isoform ($PrP^{Sc}$) of the endogenous prion protein ($PrP^C$). The existence of asymptomatic TSE carriers has led to concerns over the risk of iatrogenic TSE transmission, which has already occurred from variant Creutzfeldt-Jakob disease (vCJD) carriers. From a re-analysis of appendices samples resected from patients prior to their vCJD development, it was identified that vCJD could be detected in patient samples at least 2 years before the development of vCJD symptoms. What complicates the aspect of asymptomatic carriage is that the length of time it takes for the development of vCJD symptoms appears to be dictated by the PRNP codon 129 polymorphism (methionine (M)/valine (V)). This also makes it difficult to predict the potential level of vCJD. Recently, it has been found, through the immunohistochemical analysis of stored paraffin-embedded appendix samples identified an overall prevalence of abnormal prion in 493 per million of the population (or approximately 1/2000 are carriers). In addition, considering that so far all definite and probable cases of clinical vCJD have been homozygous for methionine at position 129, bar one possible vCJD case who was heterozygous (PRNP 129 MV), it is a concern that studies identified a higher than expected prevalence of abnormal prion cases in appendix samples of those that were homozygous for valine.

The potential implications of the asymptomatic carrier for secondary vCJD transmission drives the need for appropriate measures to prevent such transmission. Even when patients present with early vCJD symptoms, the signs of this disorder can vary significantly between patients. Compounding the difficulties for clinicians is that what appears to be non-CJD related morbidities results in misdiagnosis, in such instances diagnostic tests to aid in diagnosis would help with identification of suspected cases and minimise transmission possibilities. However, such diagnostic tests may be limited in the asymptomatic stages of disease and appropriate mild decontamination techniques can be significant to the control of spread in the hospital sector.

Ultimately, due to the delicate nature of surgical equipment the ideal prion decontaminant should work under mild conditions. However, $PrP^{Sc}$ is resistant to standard sterilisation guidelines (such as those issued by the World Health Organisation (WHO) or The Society for Healthcare Epidemiology of America (SHEA)), and practises that are advised to sterilise equipment are simply too severe. For example, some methods proposed to eliminate prion contamination, including exposure to NaOH (1N), sodium hypochlorite solution (20,000 ppm of available chlorine) or high temperature porous load autoclave, are not suitable for many delicate medical devices. A three stage destruction involving heating in 4% SDS at 100° C. followed by proteinase K digestion and then pronase digestion was proposed as a method to lower the risk of prion transmission. This process lowered vCJD signal in infected brain to an undetectable level, and it almost completely eliminated Rocky Mountain Laboratory (RML) scrapie infectivity from contaminated steel wires that were subsequently inoculated into Tg20 transgenic mice and wild-type CD-1 animals. Modified mixes such as alkaline cleaners (pH 12.2) along with mixes of 0.2% SDS and 0.3% NaOH (pH 12.8) have also been found to completely removed scrapie strain 263 infectivity. For delicate equipment, however, there is a need for more harmless approaches lacking high temperature and/or alkaline processing and the processes advised by the World Health Organisation for prion decontamination are too severe for most reusable hospital equipment. The effect of these treatments on some medical equipment have been studied and evident damage was seen on the items tested. Furthermore, a study of ready to use reusable surgical instruments identified that the level of residual protein remaining on these devices could pose a risk for the transmission of the prion agent. It has also been reported that none of the commonly used enzymatic cleaners employed in Sterile Service departments allowed for complete removal of protein or prion matter from test material. Eliminating protein load on instruments is essential not only for reducing the risk of prion transmission but also for controlling other hospital-acquired infections. There is therefore a problem with existing approaches and that is the lack of suitable processes for delicate equipment.

WO2008057293 discloses compositions and methods for prion degradation, decontamination or disinfection. The composition described comprises an oxidizing agent, one or more proteases and a surfactant such as an ionic surfactant/detergent. However, the composition requires a number of different components which would have different storage and handling requirements and/or applied in a time consuming sequential manner.

Relatively few microorganisms have been previously reported to produce a protease with the ability to degrade PrP$^{Sc}$. Müller-Hellwig et al., (2006) *Syst Appl Microbiol* 29: 165-171 describes screening over 600 bacterial isolates for protease production, of these 199 secreted a protease and only 6 were found to have some level of prion degrading activity against scrapie infected hamster brain homogenate. Hui et al., (Hui et al., (2004) *In Vitro Cell Dev Biol Anim* 40: 293-296) screened over 500 microorganisms to obtain the *Streptomyces* sp that secreted the protease E77, it degraded scrapie infected hamster brain homogenate at 60° C. and pH 11.0. Greater than 300 bacterial strains were screened to obtain the *Bacillus* sp. MSK103 protease (Yoshioka et al., (2007) *J Appl Microbiol* 102: 509-515). The ability of a protease to breakdown prion material is thought to be dependent on conditions that open up the protein structure and enable the protease to access the protein backbone. As a consequence a number of proteases have been tested for their anti-prion action at alkaline pH. The alkaline pH is also chosen as the pH itself contributes to inactivation of the prion agent.

There is also a problem with existing approaches in dealing with environmental contamination. For example in the agricultural industry, the prion agent has been detected in urine (Sc237 strain) and blood of infected animals (263K strain), and in the faeces of symptomatic and asymptomatic deer which risks the continued transmission of animal TSEs. Both scrapie of sheep and CWD of elk and deer are horizontally transmissible, and their agent can remain infectious for years in the environment.

The persistence of the prion agent within the environment and the demonstrated transmission of CJD through surgery and contaminated products emphasises the need for decontamination approaches that can be used in a safe and routine manner to limit the spread of TSEs.

It is therefore an object of the present invention to mitigate or address one or more of the above identified issues with previous prion degradation techniques. It is a further object to identify a composition which can be used for prion degradation, decontamination or disinfection. Ideally, such a composition would be functionally active at less severe conditions than previously described so that it could be used in conjunction with medical equipment and especially more delicate medical equipment. Additionally, or alternatively, the composition may be suitable for use in environmental and/or agricultural prion degradation, decontamination or disinfection. It would be desirable if the composition was relatively easy to produce, handle and use for prion degradation, decontamination or disinfection.

SUMMARY OF THE INVENTION

In accordance with a first aspect of the present invention, there is provided a composition for degrading prion material comprising a Thermitase.

The term "degrading" is intended to mean to breakdown or reduce the activity or infectivity of a prion or prion material which would otherwise have the potential to result in the neurodegeneration (or a quicker onset of neurodegeneration) in an exposed animal (including humans). The term also includes disinfection and decontamination of a substrate from prion or prion material.

Advantageously, it has been found that Thermitases can degrade prion material without additionally requiring other components such as oxidising agents or surfactants.

It is preferred that the Thermitase has the amino acid sequence of SEQ ID NO: 1 and/or SEQ ID NO: 4, or a sequence or sequences having 95% or more homology thereof. More preferably, the Thermitase has the amino acid sequence of SEQ ID NO: 1 and/or SEQ ID NO: 4, or a sequence or sequences having 97% or more homology thereof. Even more preferably, the Thermitase has the amino acid sequence of SEQ ID NO: 1 and/or SEQ ID NO: 4, or a sequence or sequences having 98% or more homology thereof. Most preferably, the Thermitase has the amino acid sequence of SEQ ID NO: and/or SEQ ID NO: 4, or a sequence or sequences having 99% or more homology thereof. Ideally, the Thermitase has the amino acid sequence of SEQ ID NO: 1 and/or SEQ ID NO: 4.

Homology may be determined using on-line homology algorithm "BLAST" program, which is currently publicly available at http://www.ncbi.nlm.nih.gov/BLAST/. Sequences which have a high degree of homology may be mutants, variants or genetically modified sequences. Deliberate alteration of amino acid sequences may be accomplished by conventional (in vitro) genetic manipulation technologies, such as gene disruption, conjugative transfer, etc. Genetic modification includes introduction of exogenous and/or endogenous DNA sequences. Natural or induced mutations may include at least single base alterations such as deletion, insertion, tansversion or other DNA modifications which may result in alteration of the amino acid sequence encoded by the DNA sequence.

The composition may further comprise a number of other constituents which are often required to aid storage and/or ensure the appropriate activity of an enzyme. Preferably, the composition further comprises a buffer. Such a buffer may be a biological buffer such as HEPES.

The composition will preferably have a pH in the range of about 6 to about 13. More preferably, the composition will have a pH in the range of about 7.5 to about 12.5. Most preferably, the composition will have a pH in the range of about 7 to about 12.

The Thermitases will preferably have a wide activity temperature range. The Thermitase will preferably be active in the range of about 10° C. to about 65° C. More preferably, the composition will be active in the range of about 15° C. to about 60° C. More preferably, the composition will be active in the range of about 15° C. to about 55° C.

The composition may be formulated in the form of a solution or is formulated so as to easy form a solution if desired. The skilled addressee will understand how various enzyme solutions can be prepared for immediate use or for subsequent dilution or rehydration. Preferably, the solution is an aqueous solution. Most preferably, the composition comprises the Thermisase component in a lyophilised activated state.

In some instances, it may be preferred that the composition comprises two or more Thermitases. This potentially increases the activity range of the composition at successfully degrading prion material. Preferably, the composition comprises Thermitases having an amino acid sequence of SEQ ID NO: 1 and SEQ ID NO: 4, or sequences having 95% or more homology thereof.

The composition of the present invention will have wide application wherever prion material requires degradation. For example, the composition may be for use in degrading prion material on medical equipment. The composition is particularly suited to delicate medical equipment which is often damaged by the use of high temperatures and/or highly alkaline sterilising products. Alternatively the composition may be for use in degrading prion material in the environment, such as agricultural land.

The composition may be in the form of a ready-made solution or spray. Alternatively, the composition may be in the form of a pre-mix solution which is for subsequently diluted or added to a liquid (such as an existing medical equipment sterilising solution) for application to degrade prion material.

In accordance with another aspect of the present invention there is provided a protease having the amino acid sequence of SEQ ID NO: 1, SED ID NO: 2, SEQ ID NO: 4, or SEQ ID NO: 5 or an amino acid sequence having 98% or more homology thereof.

More preferably, the protease has the amino acid sequence of SEQ ID NO: 1, SED ID NO: 2, SEQ ID NO: 4, or SEQ ID NO: 5 or an amino acid sequence having 99% or more homology thereof. Most preferably the protease has the amino acid sequence of SEQ ID NO: 1, SED ID NO: 2, SEQ ID NO: 4, or SEQ ID NO: 5.

The protease may be for use in degrading prions or prion material.

In accordance with yet another related invention, there is provided a method for prion degradation, decontamination or disinfection, the method comprising contacting a substrate containing and/or coated with prion material with a composition comprising one or more Thermitases.

It is preferred that the method is conducted under conditions effective to enable the activation or activity of the Thermitase to degrade prion material. Preferably, the method is conducted in the range of about 10° C. to about 65° C. and/or a pH in the range of about 6 to about 13. More preferably, the method is conducted in the range of about 15° C. to about 60° C. and/or a pH in the range of about 6.5 to about 12.5. Most preferably, the method is conducted in the range of about 10° C. to about 65° C. and/or a pH in the range of about 7 to about 12.

The Thermitase will preferably comprise the amino acid sequence of SEQ ID NO: 1, SED ID NO: 2, SEQ ID NO: 4, or SEQ ID NO: 5 or an amino acid sequence having 98% or more homology thereof. More preferably, the Thermitase comprises the amino acid sequence of SEQ ID NO: 1, SED ID NO: 2, SEQ ID NO: 4, or SEQ ID NO: 5 or an amino acid sequence having 99% or more homology thereof. Most preferably, the Thermitase comprises the amino acid sequence of SEQ ID NO: 1, SED ID NO: 2, SEQ ID NO: 4, or SEQ ID NO: 5.

In another yet related aspect of the present invention, there is a method of producing a Thermitase for use in prion degradation, the method comprising transforming a host organism with a DNA sequence comprising SEQ ID NO: 3 or SEQ ID NO: 6 or a DNA sequence having 95% or more homology thereof, and putting the DNA sequence in the host under a positive promoter control for stimulating production of a Thermitase in the host organism and harvesting said Thermitase.

The steps of transforming a host organism with DNA so as to produce the desired enzyme under positive promoter control will be commonly used recombinant genetic manipulation techniques which will be well understood by the skilled artisan.

In accordance with a further aspect of the present invention, there is provide a kit of parts for prion degradation, decontamination or disinfection, comprising:

a) a Thermitase; and
b) a buffer solution having a pH in the range of 6 to 13.

Such a kit may further comprises a container housing the Thermitase and/or buffer solution or buffer solution constituents, a means for measuring and/or mixing the correct quantities of Thermitase and/buffer solution or buffer solution constituents together so as to form a solution which can degrade prion material.

DETAILED DESCRIPTION OF THE INVENTION

Embodiments of the present invention will now be described, by way of example only, with reference to the accompanying figures, in which.

Figure 3:
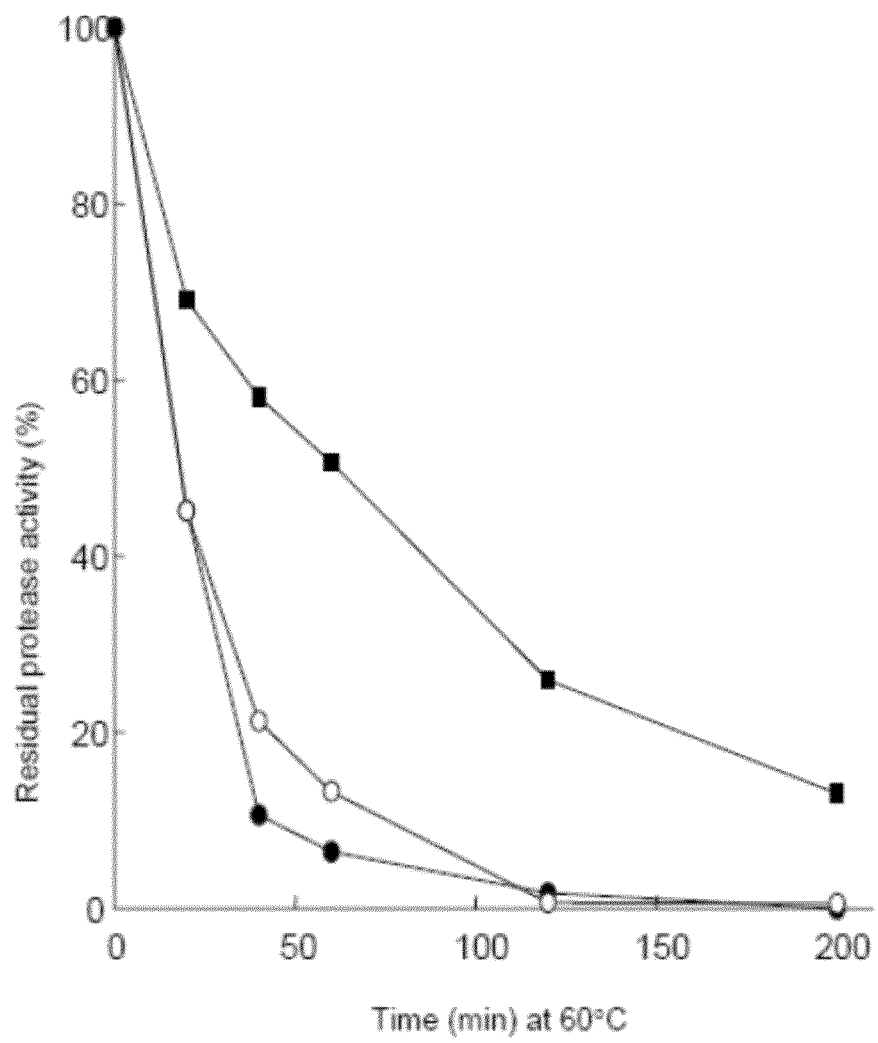
Figure 4:
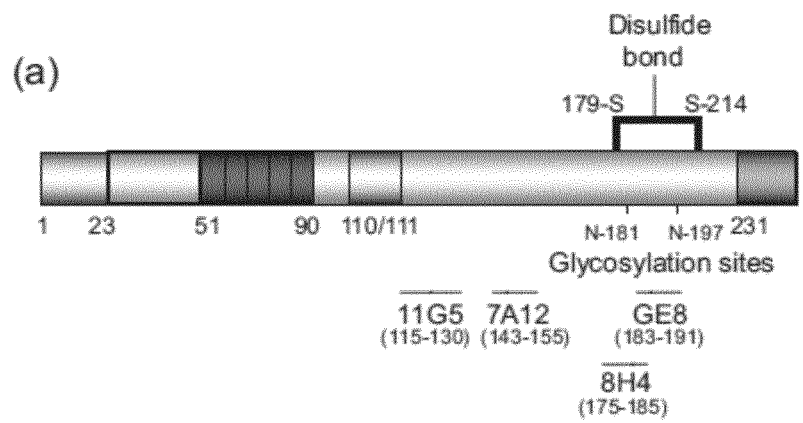
Figure 4:
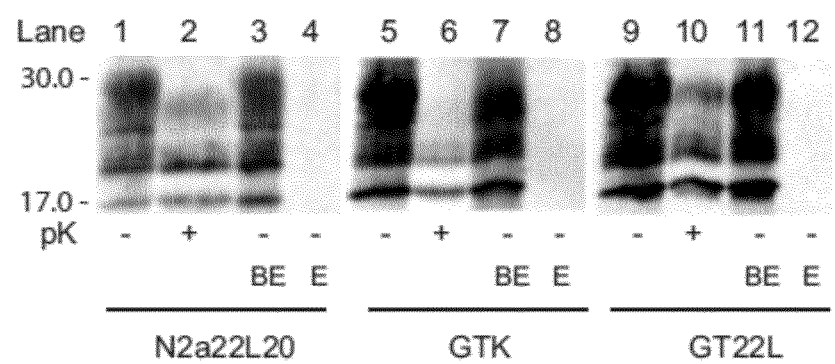
Figure 4:
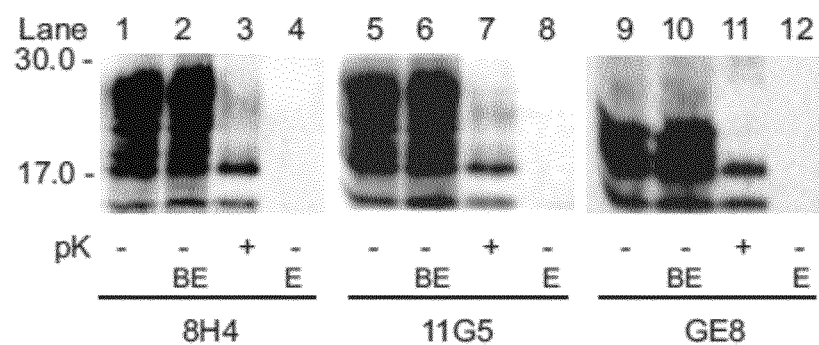
Figure 5:
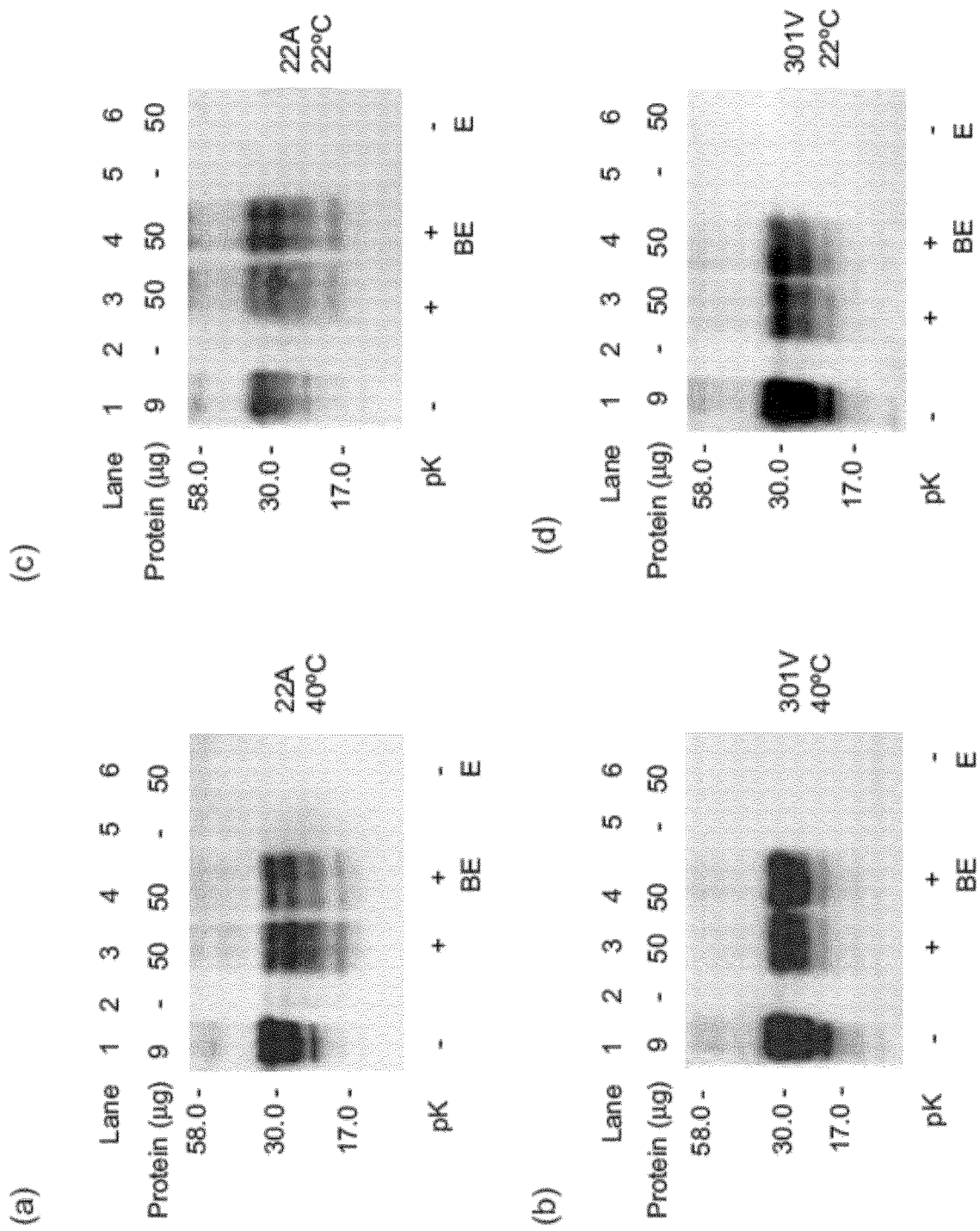
Figure 6:
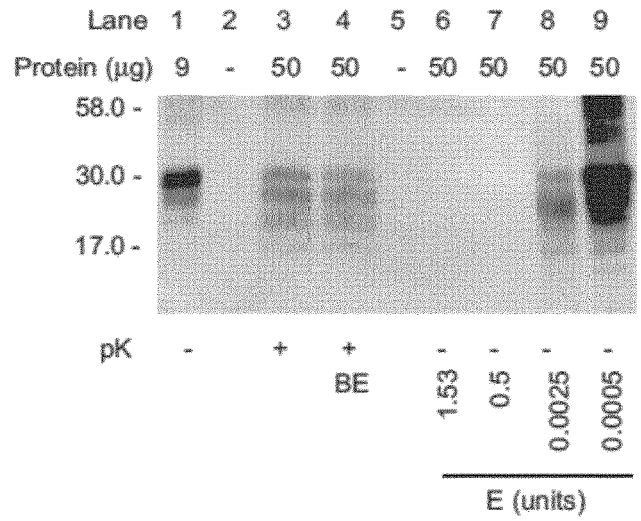
Figure 6:
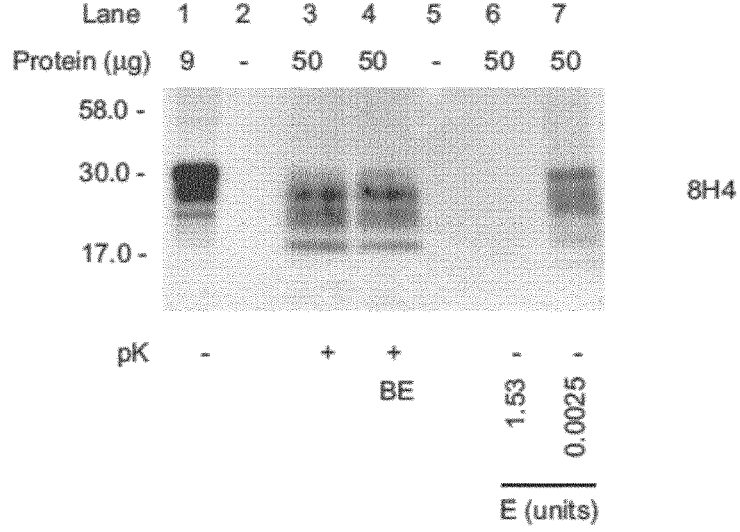
Figure 6:
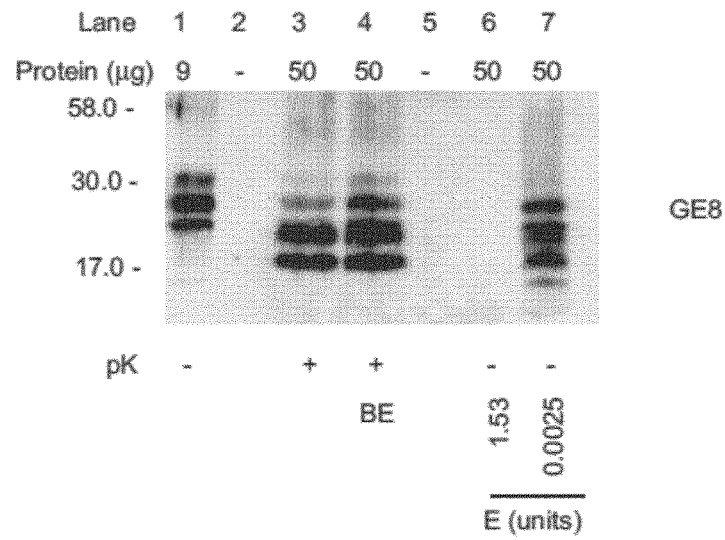
Figure 7:
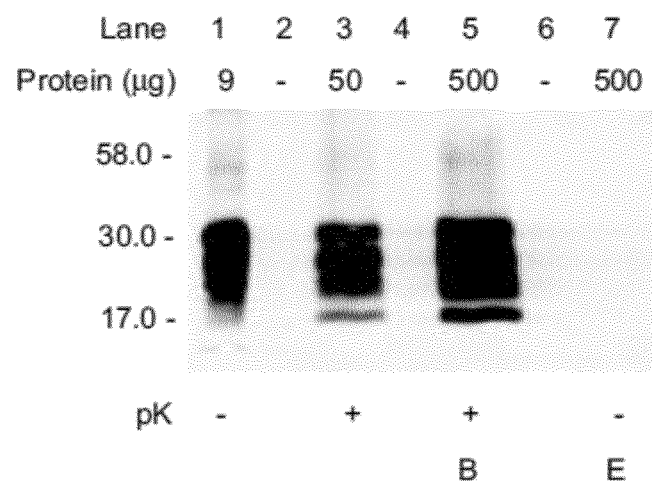
Figure 8:
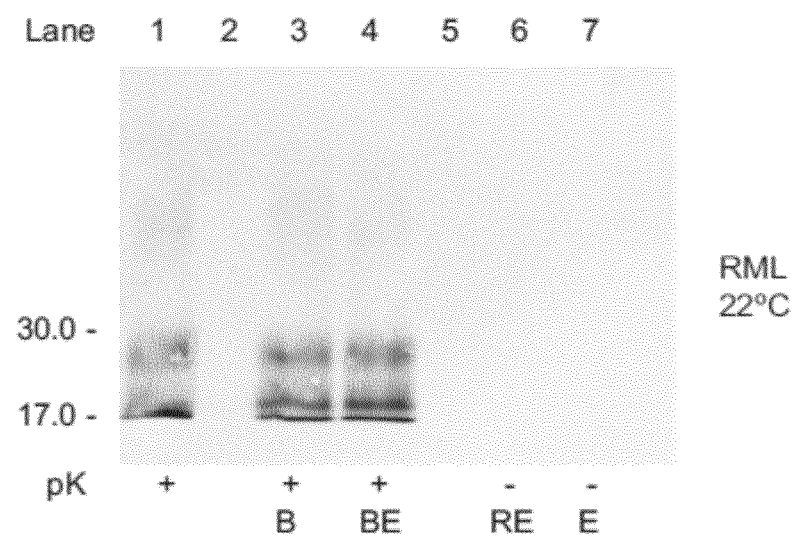
Figure 9:
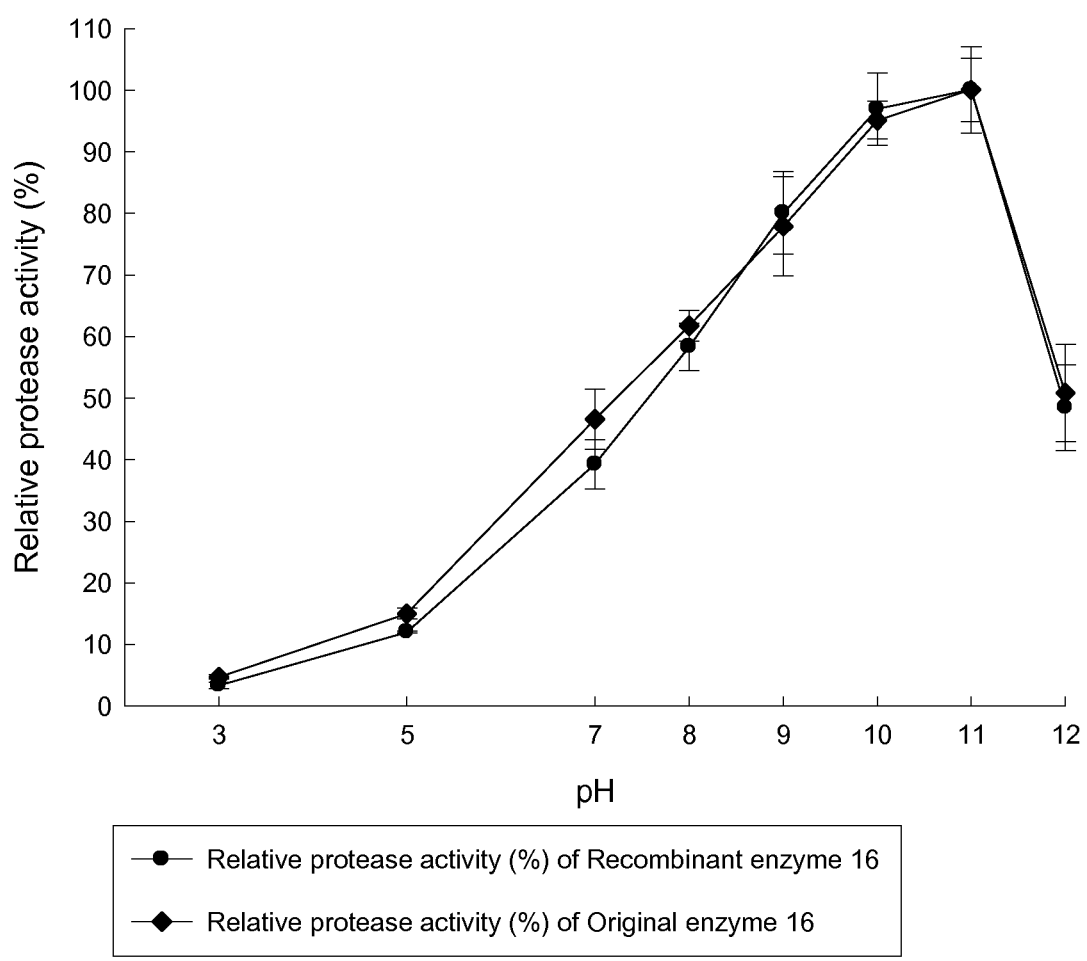

FIG. 3 is a graph showing the effect of calcium on the stability of the *Thermoactinomyces* sp. 16 protease. For the effect of calcium on the stability of the protease, the enzyme was incubated at 60° C. at pH 11.0 in CAPS buffer over the times indicated in the presence or absence of calcium. Residual protease was assayed at pH 11.0 at 40° C. (symbols denote: residual activity at 60° C.; and at 60° C. in the presence of 1 mM $Ca^{2+}$ c; or 10 mM $Ca^{2+}$);

FIG. 4 shows the profiling the degradation of $PrP^{Sc}$ when using protease 16 where: (a) is schematic diagram of Mouse PrP showing the antibodies used during the experiments; (b) shows lysates of N2a22L20, GTK and GT22L cells which were incubated in the presence of protease enzyme (E) (0.5 units/50 μg protein) or boiled enzyme (BE) in 0.1M HEPES, pH 7.0, for 15 mins at 40° C.; (c) shows lysates of N2a22L20 which were incubated in the presence of E (0.5 units/50 μg protein) or BE in 0.1M HEPES, pH 7.0, for 15 mins at 40° C. and PrP was analysed with the antibodies indicated. All samples were solvent precipitated after incubation and were analysed by SDS PAGE and immunoblotting with antibody 7A12 (b) and 8H4, 11G5 and GE8 (c). Lanes not marked by E or BE are control lysates prior to incubation, and these where indicated were treated with pK (+) at 16 μg/mg protein. 50 μg, as determined from the lysate prior to incubation, were loaded into each lane. Results are representative of three independent experiments. Molecular mass markers in kilodaltons are shown on the left of the panels;

FIG. 5 shows the degradation of prion in brain homogenate by protease 16 where 50 μg of infected brain homogenate was resuspended in HEPES buffer pH 7.0 (lane 3 of a, b, c and d) or in HEPES buffer pH 7.0 containing 1.53 units of BE (lane 4) or the protease (E) at 1.53 units/50 μg protein. BE samples and enzyme treated samples were incubated at 40° C. (a and b) or 22° C. (c and d) for 15 mins. Samples were solvent precipitated, resuspended in LB buffer and PrP levels with (+) or without (−) pK digestion were analysed. pK digestion was carried out at 16 μg pK/mg protein for 30 min. Lanes 2 and 5 are blank lanes. Samples were analysed by SDS PAGE and immunoblotting with antibody 7A12. Molecular mass markers in kilodaltons are shown on the left of the panels;

FIG. 6 shows the profiling of the degradation of the prion by protease 16 in 22A infected brain homogenate. 50 μg of infected brain homogenate was resuspended in HEPES buffer pH 7.0 (lane 3 of a, b and c) or in HEPES buffer pH 7.0 containing 1.53 units of BE (lane 4) or the enzyme units indicated. BE samples and enzyme treated samples were incubated at 22° C. for 15 mins. Samples were solvent precipitated, resuspended in LB buffer and PrP levels with (+) or without (−) pK digestion were analysed. pK digestion was carried out at 16 μg pK/mg protein for 30 min. Lanes 2 and 5 are blank lanes. Samples were analysed by SDS PAGE and immunoblotting with antibody 7A12, 8H4 and GE8. Molecular mass markers in kilodaltons are shown on the left of the panels;

FIG. 7 shows the degradation of the prion by protease 16 in 22A brain homogenate at 500 µg 22A infected brain homogenate, was resuspended in HEPES buffer pH 7.0 (lanes 3 and 5) or in HEPES buffer pH 7.0 containing 1.53 units E/50 µg protein (lane 7). Enzyme treated samples were incubated at 22° C. for 15 mins. Samples were solvent precipitated, resuspended in LB buffer and PrP levels with (+) or without (−) pK digestion were analysed. pK digestion was carried out at 16 µg pK/mg protein for 30 min. Lanes 2, 4 and 6 are blank lanes. Samples were analysed by SDS PAGE and immunoblotting with antibody 7A12. Molecular mass markers in kilodaltons are shown on the left of the panels;

FIG. 8 shows the degradation of prion by recombinant protease 16 in RML brain homogenate. 50 µg RML infected brain homogenate, was resuspended in 0.1M HEPES buffer pH 7.0 (lane 3) or in 0.1M HEPES buffer pH 7.0 containing boiled enzyme (BE) (lane 3) or 0.5 units recombinant enzyme (RE)/50 µg protein (lane 6) or 0.5 units non recombinant enzyme (E) (lane 7). Enzyme treated samples were incubated at 22° C. for 15 mins. Samples were solvent precipitated, resuspended in LB buffer and PrP levels with (+) or without (−) pK digestion were analysed. pK digestion was carried out at 16 µg pK/mg protein for 15 min. Lanes 2 and 5 are blank lanes. Samples were analysed by SDS PAGE and immunoblotting with antibody 7A12. Lane 1 shows 50 µg RML brain homogenate which has been treated with LB buffer and digested with pK as above. Molecular mass markers in kilodaltons are shown on the left of the panels;

FIG. 9 is a graph showing the effect of pH on protease activity of the original and recombinant proteinase 16. The original and recombinant proteinase 16 were assayed using BSA (1%, w/v) as substrate in 0.1M Universal buffer at the pH values indicated for 30 min at 40 C;

FIG. 10 shows an amino acid alignment between the mature amino acid sequences of protease 16 (SEQ ID NO: 1) and protease 10 (SEQ ID NO: 4);

FIG. 11 shows an amino acid alignment between the complete signal (pro-domain and mature) amino acid sequences of protease 16 (SEQ ID NO: 2) and protease 10 (SEQ ID NO: 5);

FIG. 12 shows an amino acid alignment between the amino acid sequences of protease 16 (SEQ ID NO: 2) and a thermitase precursor (*Laceyella sacchari*) (SEQ ID NO: 20);

FIG. 13 shows an amino acid alignment between the amino acid sequences of protease 10 (SEQ ID NO: 5) and a thermitase precursor (*Laceyella sacchari*) (SEQ ID NO: 20);

FIG. 14 shows a nucleotide alignment between the mature gene sequences of protease 16 (SEQ ID NO: 3) and protease 10 (SEQ ID NO: 17);

FIG. 15 shows a nucleotide alignment between the gene sequences of protease 16 (SEQ ID NO: 22) and protease 10 (SEQ ID NO: 6);

FIG. 16 shows a nucleotide alignment between the gene sequences of protease 16 (SEQ ID NO: 3) and a thermitase precursor (*Laceyella sacchari*) (SEQ ID NO: 21); and FIG. 17 shows a nucleotide alignment between the gene sequences of protease 10 (SEQ ID NO: 6) and a thermitase precursor (*Laceyella sacchari*) (SEQ ID NO: 21).

ISOLATION AND PURIFICATION OF A NEW MICROBIAL PROTEASE CAPABLE OF DEGRADING PRIONS

A number of historical University College Dublin microbial isolates were screened for enzyme systems with the ability to degrade pK resistant PrP (PrP$^{Sc}$) under mild conditions. Initially *Bacillus* and Actinomycete spp were screened for protease activity, of those that were screened both the thermophilic actinomycete 16 and 10 were found to have protease producing abilities.

Screening Programme to Identify Protease Producing Bacterium

The Thermoactinomycete sp. 16 was selected after a screening programme of a range of *Bacillus* sp and Actinomycetes. Table 1 below shows the results for investigating protease producing *Bacillus* isolates.

TABLE 1

| *Bacillus* isolate | CFS pH | | | Protease activity (units/ml) | | |
|---|---|---|---|---|---|---|
| | 6 h | 24 h | 48 h | 6 h | 24 h | 48 h |
| Z1135 | 7.6 | 8.7 | 9.2 | 0 | 0 | 0 |
| S1241 | 7.9 | 8.8 | 9.1 | 0 | 0 | 0 |
| S1232 | 7.9 | 8.9 | 9.1 | 0 | 0 | 0 |
| Z1134 | 7.7 | 5.6 | 5.4 | 0 | 0 | 0 |
| Z1133 | 8.0 | 8.9 | 8.9 | 0 | 0 | 0 |
| T1223 | 7.5 | 5.7 | 5.4 | 0 | 0 | 0 |
| S1226 | 7.9 | 9.0 | 8.7 | 0 | 0 | 0 |
| D1228 | 7.9 | 9.1 | 8.9 | 0 | 0 | 0 |
| Z1136 | 7.6 | 5.6 | 5.4 | 0 | 0 | 0 |
| S1231 | 8.1 | 8.8 | 8.6 | 0 | 0 | 0 |
| Z1139 | 7.2 | 8.9 | 8.8 | 0 | 0 | 0 |
| Z1140 | 9.0 | 5.7 | 5.7 | 0 | 0 | 0 |
| X1229 | 5.0 | 4.7 | 4.7 | 0 | 0 | 0 |
| T1222 | 5.2 | 5.5 | 9.0 | 0 | 0 | 0 |
| S1226 | 6.0 | 4.7 | 4.8 | 0 | 0 | 0 |
| Z1150 | 7.8 | 9.1 | 8.7 | 0 | 0 | 0 |
| S1210 | 7.7 | 5.9 | 5.6 | 0 | 0 | 0 |
| D1111 | 4.7 | 4.7 | 4.8 | 0 | 0 | 0 |
| S1197 | 7.1 | 9.2 | 8.8 | 0 | 0 | 0 |
| JF 40 | 7.1 | 8.9 | 8.9 | 0 | 0 | 0 |
| T1224 | 7.7 | 5.6 | 5.6 | 0 | 0 | 0 |
| 55 | 6.3 | 4.8 | 4.8 | 0 | 0 | 0 |
| 38 | 8.2 | 8.8 | 9.2 | 0 | 0 | 0 |
| 193 | 6.9 | 6.9 | 8.7 | 0 | 0 | 0 |
| 94 | 7.7 | 5.7 | 5.6 | 0 | 0 | 0 |

The isolates were grown at 200 rpm at 55° C. up to 48 h. The CFS was assayed for protease activity using BSA (1% w/v) in 0.1M phosphate buffer pH 7.0.

Table 2 below details the screening and selection of protease producing Actinomycete isolates.

TABLE 2

| Actinomycete Isolate | Growth Temp (° C.) | CFS pH | | | Protease activity (units/ml) | | |
|---|---|---|---|---|---|---|---|
| | | 6 h | 24 h | 48 h | 6 h | 24 h | 48 h |
| V1105 | 55° C. | 7.2 | 6.8 | 6.3 | 0 | 0 | 0 |
| V1115 | 37° C. | 7.6 | 8.2 | 9.3 | 0 | 0 | 0 |
| V1104 | 37° C. | 7.2 | 7.3 | 8.3 | 0 | 0 | 0 |
| V1103 | 37° C. | 7.1 | 7.1 | 6.3 | 0 | 0 | 0 |
| V1106 | 37° C. | 7.1 | 7.1 | 6.7 | 0 | 0 | 0 |
| L1198 | 55° C. | 7.9 | 8.7 | 9.3 | 0 | 0 | 0 |
| *Streptomyces aminophilus* | 37° C. | 7.6 | 8.3 | 9.0 | 0 | 0 | 0 |
| *Thermoactinomyces* sp. 10 | 55° C. | 8.4 | 8.7 | 8.4 | 0.1 | 0.2 | 0.1 |
| *Thermoactinomyces* sp. 16 | 55° C. | 7.2 | 8.1 | 9.3 | 0 | 0.2 | 0.2 |

As can be seen from Table 2, of the micro-organisms screened, protease production was only seen in two *Thermoactinomyces* sp. No 10 and 16. Both of these species were isolated. Although the actinomycetes are known for their enzyme production, not all produce proteases. Thermoac-

Figure 1:
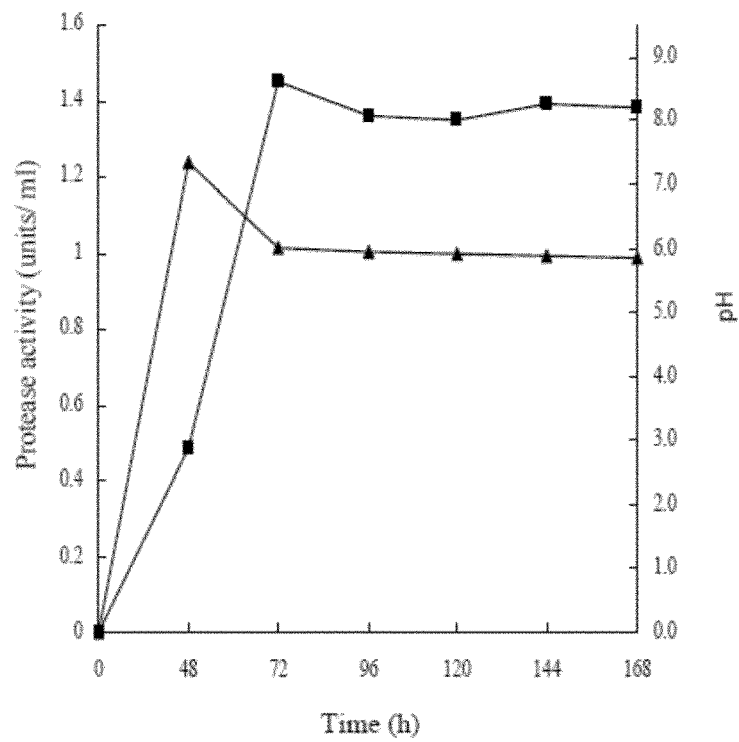
FIG. 1 is a graph showing the enzyme production by *Thermoactinomyces* sp. 16 (symbols denote: pH (▲); and protease activity (units/ml) (■))

*tinomyces* sp. 16 was chosen initially for further work over *Thermoactinomyces* sp. 10 as its enzyme levels in the cell free supernatant (CFS) were maintained between 24 and 48 h in the screening studies, potentially indicating better enzyme stability. When conditions of enzyme production from *Thermoactinomyces* sp. 16 at 40° C. were optimised, maximal enzyme levels were produced at 72 h growth and these levels were maintained for at least up to 168 hours (as shown in FIG. 1).

The first potential candidate protease was identified from a *Thermoactinomyces* isolate sp 16 and was denoted protease 16. Protease 16 was later characterised as a Thermitase. This protease was found to have the ability to degrade pK resistant prion material under mild conditions and allowed for complete loss of detectable prion signal from 50 µg protein, and it did so within 15 min at 22° C.

The Thermoactinomycete isolates 10 and 16 were isolated from mushroom compost using International *Streptomyces* Project medium no. 4 (ISP4). *Thermoactinomyces* sp. 16 and 10 are Gram-positive bacterium. The organisms grew on a nutrient agar ((g/l) soluble starch, 10.0; Lab-lemco agar, 23.0; yeast extract, 2.0, pH7.2)) forming colonies that were initially firm compact and leathery. The colonies were then completely covered with aerial mycelium, which was velvety in texture and colonies displayed sectoring similar to that of *Streptomyces griseus*. The reverse side of colonies on the nutrient agar and ISP4 were brown/yellow and brown, respectively. Light microscopy revealed the aerial mycelium consisted of straight to flexuous spore chains consisting of greater than 12 arthrospores. The actinomycete isolate was identified as belonging to the Thermoactinomycetes by virtue of the isolates macroscopic and microscopic characteristics. The thermophilic nature identifies them as Thermoactinomycetes.

A deposit of the *Thermoactinomyces* sp 16 strain was made at the National Collections of Industrial and Marine Bacteria Limited (NCIMB) Ferguson Building, Craibstone Estate, Bucksburn, Aberdeen, AB21 9YA, Scotland, UK on Aug. 18, 2010 and accorded the accession number NCIMB 41754.

The protease of a second *Thermoactinomyces* sp isolate sp 10, which produced a protease denoted 10 was found to also degrades the prion within 15 min at 22° C.

Protease Production

The microbial isolate 10 and 16 were maintained at 4° C. on slopes of nutrient agar containing 1% (w/v) starch at pH 7.0. To produce the protease, a standard inoculum was developed by transferring a loopful of culture to 50 ml inoculum medium (g/l): soluble starch 30.0, bacto-peptone 5.0, yeast extract 5.0, $CaCl_2 2H_2O$, 0.5, $MnCl_2 4H_2O$ 0.5, $MgCl_2 6H_2O$ 0.48, $KH_2PO_4$ 1.0, pHi 7.0. The culture was grown for 48 h at 55° C. and 200 rpm. 5% (v/v) standard inoculum was transferred to 50 ml production medium (g/l): maltose 30.0, bacto-tryptone 5.0, yeast extract 5.0, $CaCl_2 2H_2O$ 0.5, $MnCl_2 4H_2O$ 0.5, $MgCl_2$ $6H_2O$ 0.48, $KH_2PO_4$ 1.0, pHi 7.0. The cells were then grown at 40° C. and 200 rpm for 72 h. Cells were then removed from the culture by centrifugation at 10,000 g for 15 min. The protease activity in the cell-free supernatant was then determined.

Purification of the Protease 16

The secreted protease was purified from cell free supernatant by $(NH_4)_2SO_4$ (0-60%) fractionation followed by affinity chromatography on Bacitricin-Sepharose 4B according to the quantities shown in Table 3 below.

TABLE 3

| Purification Step | Specific activity (units/mg protein) | Purification (X-fold) | Recovery (%) |
|---|---|---|---|
| Cell free supernatant | 0.05 | 1 | 100 |
| $(NH_4)_2SO_4$ (0-60%) fractionation | 0.79 | 14.6 | 69.9 |
| Bacitricin-Sepharose 4B | 3.56 | 65.9 | 50.1 |

The first step was ammonium sulphate (0-60%) fractionation. To express the final ammonium sulphate concentration as % ammonium sulphate saturation the Green and Hughes calculations were used. The precipitate obtained after fractionation was suspended in 0.02M HEPES buffer, pH 7.0 and was dialysed against water for 24 h. The second step used was affinity chromatography on bacitracin-Sepharose 4B using a modification of the method of Stepanov and Rudenskaya. Bacitracin-Sepharose 4B was equilibrated with 0.04M Tris/HCL, pH 7.9. Enzyme solution in 0.04M Tris/HCL pH 7.9 was applied to the column and the column was washed with the same buffer to remove all unbound protein. The protease was then eluted from the column with 25% (v/v) propan-2-ol in 0.04M Tris/HCL pH 7.9, containing 1M NaCl at a flow rate of 0.5 ml/min. The propan-2-ol and NaCl were removed from the protease solution by dialysis.

Protease Assay

In the protease assay, activity was determined by the addition of 50 µl enzyme to 50 µl bovine serum albumin (BSA) (1%, w/v) in 0.1M CAPS buffer, pH 11.0 and incubated for 30 min at 40° C. The reaction was then stopped by the addition of 200 µl 5% (w/v) trichloroacetic acid (TCA). After 10 min the precipitate was centrifuged at 3,000 g for 10 min. Total protein concentration in the supernatant was measured using the bicinchoninic acid (BCA) protein assay kit (Sigma). A unit of activity was defined as the amount of enzyme releasing 1 mg TCA soluble protein fragments from BSA in 30 min at 40° C.

Protease Characterisation

Figure 2:
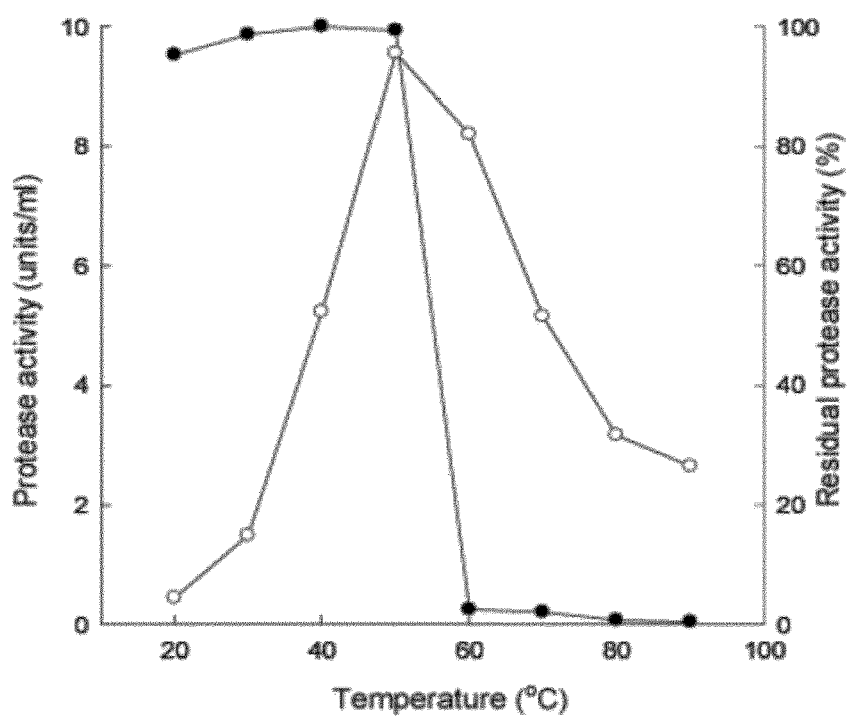
FIG. 2 is a graph showing the effect of temperature on the activity and stability of the *Thermoactinomyces* sp. 16 protease, the protease assay was carried out at temperatures from 20-90° C. For stability to temperature, the enzyme was incubated at each temperature for 1 h and residual activity was determined at 40° C. at pH 11.0 (symbols denote activity profile c; stability profile z)

For determination of the effect of pH on enzyme activity the protease assay was carried out using BSA (1%, w/v) prepared in 0.1M Briton and Robinson's Universal buffer; pHs 2.0-12.0 and the assay was performed as above. As shown in Table 3, recovery of approximately 50% after purification was achieved. From a pilot scale shaker flask production from one run resulted in a yield of 3000 units, after purification this would reduce to 1500 units. The purified protease was an alkaline protease with optimal activity towards pH 11.0 and it displayed highest resistance to pHs between pH 8.0 and 11.0. The enzyme was optimally active at 50° C. and exhibited high stability up to 50° C. after 1 h exposure (as shown in FIG. 2b). To identify the family of proteases to which this enzyme belongs, the purified protease was exposed to 10 mM specific inhibitors and the results shown in Table 4 below.

TABLE 4

| Reagent | Protease target | Residual protease activity (% of control, no reagent) (10 mM) |
|---|---|---|
| Bestatin | Amino peptidase | 92.6 |
| Ethylenediaminetetraacetic acid | Metalloprotease | 99.6 |
| Leupeptin | Serine and thiol protease | 56.8 |

TABLE 4-continued

| Reagent | Protease target | Residual protease activity (% of control, no reagent) (10 mM) |
|---|---|---|
| Pepstatin | Acid protease | 97.6 |
| Pefabloc | Serine protease | 2.9 |
| Phenylmethylsulfonyl fluoride | Serine protease | 5.4 |

Both pefabloc and phenylmethylsulfonyl fluoride significantly inhibited the enzyme, this would suggest that the protease belongs to the serine alkaline protease family. For stability of the enzyme preliminary data with calcium has identified that calcium can stabilise the protease (as shown in FIG. 3). This demonstrated that the enzyme could be stabilised and that specific calcium binding amino acid complexes contributing to the proteins stability may be targeted genetically to improve the stability characteristics of this enzyme further.

Cell Culture

The neuroblastoma cell line infected with the 22 L scrapie strain (N2a22L20) was used (Prior et al., (2007) *J Virol* 81: 11195-11207). The N2a22L20 cells were grown in DMEM medium supplemented with 10% FCS, 10 mM penicillin-streptomycin and 300 μg/ml geneticin. GT1 cells infected with the chandler scrapie isolate (GTK) and the 22 L scrapie strain (GT22L) (Nishida et al., (2000) *J Virol* 74: 320-325), were maintained in DMEM medium supplemented 5% FCS, 5% HS, 1 mM Sodium Pyruvate and penicillin-streptomycin. Cells were maintained at 37° C. in an atmosphere of 5% $CO_2$ and 95% air. For standard lysis, cells were lysed in cold lysis buffer (LB) (0.5% (v/v) Triton X-100, 0.5% (w/v) sodium deoxycholate, 150 mM NaCl and 50 mM Tris-HCl (pH 7.5), 1 μg/ml pepstatin, 1 μg/ml leupeptin, 2 mM EDTA) and total protein concentration was measured using the BCA protein assay.

Western Blotting

For $PrP^{Sc}$ analysis, lysates prepared to 50 μg were digested with 16 μg of proteinase K (pK)/mg of protein at 37° C. for 15 min, or as indicated, the reaction was then stopped with 1 mM pefabloc. Samples in loading buffer were boiled for 5 min and loaded onto 12% SDS-PAGE and analysed by western blotting employing standard techniques. For $PrP^C$ and or total PrP analysis, lysates were not pK digested. PrP was detected by incubating immunoblots with the antibodies indicated in the text followed by a horseradish peroxidase secondary antibody and developed by enhanced chemiluminescence (ECL).

$PrP^{Sc}$ Degradation from Cells

For the non-cell assay, confluent cells were lysed into cold Lysis buffer (LB) lacking protease inhibitors, lysate was then adjusted to the protein concentration and pH indicated in the text. Enzyme (E) or heat denatured boiled enzyme (BE) was added to the lysate and the final buffer concentration in the lysate was 0.1M. Samples were incubated at 40° C. for the times indicated and were then solvent precipitated and examined for PrP levels.

Degradation of Prion in Brain Homogenate

Brain homogenate (10%, w/v), from Tga20 mice infected with the 22A scrapie strain and the BSE 301V strain, were prepared by passing the brain successively through 18, 20 and 23 gauge needles in PBS until free flowing. Infected brain homogenate was then resuspended in HEPES buffer pH 7.0, or in HEPES buffer pH 7.0 containing the units of E indicated or 1.53 units BE. BE samples were incubated for 15 min, E treated samples were incubated for the times indicated, in both cases the temperature of incubation is as stated in the text. Samples were then solvent precipitated, pellets were resuspended in LB buffer (0.5% (v/v) Triton X-100, 0.5% (w/v) sodium deoxycholate, 150 mM NaCl and 50 mM Tris-HCl (pH 7.5), 1 μg/ml pepstatin, 1 μg/ml leupeptin, 2 mM EDTA) and left on ice for 20 min. Where brain homogenate was pK (+) digested the homogenate was treated with 16 μg of proteinase K (pK)/mg protein for 30 min at 37° C. Samples were then analysed for PrP levels.

Degradation of $PrP^{Sc}$ from Infected Cell Systems by Protease 16

Initial work on the ability of protease 16 to degrade the prion was carried out with the antibodies 11G5, 7A12, GE8, 8H4, that are directed to the carboxyl (C) terminus of the prion protein (as shown in FIG. 4*a*). We chose degradation conditions of pH 7.0 and 40° C. and analysed the loss of prion material from infected homogenised cells. While the protease 16 is optimally active at alkaline conditions, our ultimate aim was to obtain a degradation system working under mild conditions and at the assay pH of pH 7.0 the protease still retains significant activity. Exposure of lysates from each of the infected cell lines N2a22L20, GTK and GT22L to protease 16 for 15 min at pH 7.0 and 40° C. resulted in a complete loss of detectable PrP ($PrP^C$ and $PrP^{Sc}$) by western blot with the antibody 7A12 (as shown in FIG. 4*b* lanes 4, 8, 12 compare with lanes 2, 6 and 10, respectively). This loss was not seen when lysates were treated with inactive boiled enzyme (as shown in FIG. 4*b* lanes 3, 7 and 11).

In case proteolysis resulted in just the loss of the 7A12 epitope or in the production of prion fragments that were not detected with 7A12, immunodetection was also carried out with the antibodies 8H4 (epitope 175-185 on Mouse PrP), 11G5 (epitope 115-130) and GE8 (epitope 183-191). No signal was obtained with any of these antibodies after the N2a22L20 lysate was digested with the protease 16 (E) (as shown in FIG. 4*c* lanes 4, 8 and 12). It should be noted that the antibody GE8 could not detect highly glycosylated PrP (as shown in FIG. 4*c* lanes 9 and 10). Most likely its epitope, which is located between both glycosylation sites, is masked by complete glycosylation of the prion. This antibody appears to react in a similar manner to the antibody 6G9 and its epitope like GE8s is located around the site of glycosylation and likewise 6G9 preferentially detected mono and di-glycosylated PrP.

Degradation of Prion Material from Infected Brain Homogenate by Protease 16

To profile the prion degradation ability of protease 16, its ability to degrade prion infected brain homogenate was examined. We chose mouse adapted scrapie strain 22A and BSE strain 301V, which had been passaged in Tga20 mice. Infected brain material was homogenised directly into HEPES buffer pH 7.0 and detergents were not added. Protease 16 degraded both 22A (as shown in FIG. 6*a* lane 6) and 301V (as shown FIG. 6*b* lane 6) brain material within 15 min at 40° C. and pH 7.0. To challenge the degradation process further the temperature of degradation was dropped to 22° C. Again a complete loss of prion signal for both strains was observed (as shown in FIGS. 6*c* and *d*, respectively, lane 6).

From studies on the resistance of prion strains to thermoinactivation 22A has been shown to be one of the more resistant scrapie strains. Its passage in mice of differing Sinc genotype has little effect on resistance properties. However, Sinc genotype significantly affects the resistance characteristics of 301V. Passage of 301V for example in C57BL mice ($Prnp^{aa}$/SV) results in a BSE strain that is less thermoresistant than 22A/SV. In light of this, in terms of potential resistance properties, the profile of degradation of the protease was examined further with 22A. Although protease degradation of PrP$^{Sc}$ from the cell lines did not result in the detection of prion fragments (as shown in FIG. 4), it was assessed to ensure that this was also the case for degraded brain homogenate. The loss of 22A PrP$^{Sc}$ signal was profiled using a range of protease dilutions with the antibodies 7A12, 8H4 and GE8 (as shown in FIG. 6). With antibody 7A12 no residual bands were seen after 0.5 units of protease/50 µg brain protein were used, fragments were only seen when protease levels were dropped to 0.0025 units, and these fragments were distinct from those seen on digestion of the prion with pK, indicating that protease 16 cleaves the prion at sites different to pK (as shown in FIG. 6a). With antibodies 8H4 and GE8, only 1.53 units and 0.0025 units were used (as shown in FIG. 6b-c). As with 7A12 no fragments were observed with either 8H4 or GE8 with 1.53 units of protease, fragments could only be seen on lowering the enzyme level to 0.0025 units (as shown in FIG. 6b-d). As with 7A12 at 0.0025 units of protease the banding pattern produced with 8H4 and GE8 was distinct from that seen on pK digestion, this would indicate that the protease is digesting at different positions along the prion.

Finally, to enhance the ability to detect prion fragments, if fragments were produced after digestion with 1.53 units enzyme, the protein load was increased 10 fold (as shown in FIG. 7). 500 µg of protein was treated with 1.53 units enzyme/50 µg 22A brain protein and again the prion signal was completely lost (as shown in FIG. 7, lane 7).

The protease 16 was found to be optimally active above pH 8.0. Despite its alkaline nature it still retains activity at mild pH's and could breakdown PrP$^{Sc}$ at pH 7.0. The degradation of PrP$^{Sc}$ seen at this pH would relate to the protease itself, if the assay were carried out at pH11-12 the alkaline pH would have contributed to the loss in PrP$^{Sc}$ seen. Nonetheless, the alkaline profile of this system could lend to the incorporation of this protease into detergent systems if required. In searching for a successful antiprion protease the challenge is to obtain an enzyme system, with the right substrate specificity, to breakdown the prion into non-infectious units. The experiments had successfully identified that protease 16 can degrade PrP$^{Sc}$, under mild conditions, to undetectable levels by western blot. The enzyme degraded both 22A and 301V from mouse brain homogenate at pH 7.0 within 15 min at both 40° C. and 22° C. This provides a strong indication that this enzyme has the potential to act as an environmental decontaminant.

Isolation and Purification of a Second Microbial Protease Capable of Degrading Prions.

Later studies also identified a second candidate protease, again identified from a Thermoactinomycete isolate 10 and this was denoted protease 10. Protease 10 was also later characterised as a Thermitase.

Characterisation of Protease 16

Protease 16 was cloned and heterologously expressed in a *Lactococcus lactis* host. The protease was later identified as a Thermitase and was found to maintain its ability to degrade the prion under mild conditions which would enable it ultimately to act as a mild prion decontaminant.

Cloning of the *Thermoactinomyces* sp 16 Protease

The *Thermoactinomyces* sp 16 enzyme responsible for the degradation of PrP$^{Sc}$ under mild conditions was identified as a Thermitase (EC 3.4.21.66) after analysis by Mass spectrometry. The protease was then cloned from *Thermoactinomyces* sp 16 chromosomal DNA using a method adapted from Nikodinovic et al., (2003) *Biotechniques* 35:932-934, 936. *Thermoactinomyces* sp 16 was grown on nutrient agar containing 1% (w/v) starch, pH 7.0 at 55° C. A loop full of spores and mycelia were inoculated into 50 ml medium (g/l): soluble starch 30.0, bacto-peptone 5.0, yeast extract 5.0, CaCl$_2$2H$_2$O, 0.5, MnCl$_2$4H$_2$O 0.5, MgCl$_2$6H$_2$O 0.48, KH$_2$PO$_4$ 1.0, pHi 7.0. The culture was grown for 48 h at 55° C. and 200 rpm. 5% (v/v) of this culture was transferred to 50 ml production medium (g/l): maltose 30.0, bacto-tryptone 5.0, yeast extract 5.0, CaCl$_2$2H$_2$O 0.5, MnCl$_2$4H$_2$O 0.5, MgCl$_2$ 6H$_2$O 0.48, KH$_2$PO$_4$ 1.0, initial pH (pHi) 7.0. The cells were then grown at 40° C. and 200 rpm for 48 h. Cells were then removed from the culture by centrifugation at 10,000 g for 15 min. The pellet was dissolved in 10 ml of lysis buffer (25 mM Tris-HCl pH 7.5, 25 mM EDTA, 0.3 M sucrose, 50 µg/ml RNase A). To this 2 mg/ml Lysozyme and 1 mg/ml of Achromopeptidase were added and then incubated for 60 min at 37° C. at 200 rpm. 1% (w/v) SDS and 0.5 mg/ml Proteinase K were then added and incubated for 1.5 h at 55° C. at 200 rpm. 1/3 Vol of 5M NaCl was then added. The sample then underwent the Phenol/Chloroform/Isoamyl extraction twice, followed by isopropanol precipitation.

The gene encoding the Thermitase was PCR amplified using Thermitase FL-Sapl F and Thermitase FL-Xhol R as detailed in Table 5 below.

TABLE 5

| Primer | Sequence |
|---|---|
| Thermitase FL-Sapl F | CTCGATGCTCTTCCGCAATGAAGAAACGCGTTTCCCT [SEQ ID NO: 7] |
| Thermitase FL-Xhol R | CTCGAGTTAGTACTGAACAGCTTTGTAAGCG [SEQ ID NO: 8] |
| Thermitase ΔN-sapl | CTCGATGCTCTTCCGCAGAGGAAGTAGATAGCCAAGCGG [SEQ ID NO: 9] |

DNA Taq polymerase from Thermo scientific was used, whereas dNTPs were from Kapa Biosystems. The 1.16 kb product, using the restriction enzymes Sapl and Xhol was ligated to pAMJ2008, a high copy vector with its own signal peptide SP310mut2(9) and transformed into *Escherichia coli* DH5a. The full sequence was obtained through DNA sequencing. The Thermitase gene lacking the N-terminal signal peptide was generated by PCR amplification of the gene using the primer combination Thermitase ΔN-sapl F and Thermitase FL-Xhol R (see Table 2 above). This product was cloned into pAMJ2008, and transformed into *E. coli* DH5a in which the plasmid was developed. The entire plasmid containing the Thermitase gene lacking its signal peptide was subsequently cloned into *L. lactis* strain MG1363 generating *L. lactis* strain 16. *Lactococcus lactis* strain MG1363 and vector pAMJ2008 were both from Bioneer. The final sequence was confirmed by DNA sequencing.

Non Recombinant Protease Production

To produce the non-recombinant protease of Thermoactinomycete sp. 16, a standard inoculum was developed by transferring a loopful of spores and mycelia to 50 ml inoculum medium (g/l): soluble starch 30.0, bacto-peptone 5.0, yeast extract 5.0, CaCl$_2$2H$_2$O, 0.5, MnCl$_2$4H$_2$O 0.5, MgCl$_2$6H$_2$O 0.48, KH$_2$PO$_4$ 1.0, pHi 7.0. The culture was grown for 48 h at 55° C. and 200 rpm. 5% (v/v) standard inoculum was transferred to 50 ml production medium (g/l): maltose 30.0, bacto-tryptone 5.0, and yeast extract 5.0, CaCl$_2$2H$_2$O 0.5, MnCl$_2$4H$_2$O 0.5, MgCl$_2$ 6H$_2$O 0.48, KH$_2$PO$_4$ 1.0, pHi 7.0. The cells were then grown at 40° C. and 200 rpm for 72 h. Cells were then removed from the culture by centrifugation at 10,000 g for 15 min. The protease activity in the cell-free supernatant was then determined.

Recombinant Protease Production

To produce the recombinant protease of Thermoactinomycete sp. 16a standard inoculum of *L. lactis* stain 16 was developed by transferring 200 µl of frozen stock of *L. lactis* stain 16 (OD600 nm of 1) into 5 ml of production media (g/l): M17 broth 42.0, Glucose 10.0, Yeast Extract 20.0 and 1 ug/ml erythromycin. The culture was grown for 18 h at 30° C., and 200 rpm. 1 ml of inoculum (OD600 nm of 1) was transferred to 50 ml of production medium. The culture was grown for 8 h at 30° C., pH6.5 and 200 rpm. The culture was maintained at pH 6.5 by the addition of 3M KOH at identified time periods. Cells were then removed from the culture by centrifugation at 10,000 g for 15 min 4° C. The protease activity in the cell-free supernatant was then determined.

Purification of Protease

The protease of Thermoactinomycete sp 16 was purified from the cell-free supernatant in two steps. The first step was ammonium sulphate (0-60%) fractionation. To express the final ammonium sulphate concentration as % ammonium sulphate saturation the Green and Hughes calculations were used. The precipitate obtained after fractionation was suspended in 0.02M HEPES buffer, pH 7.0 and was dialysed against water for 24 h. The second step used was affinity chromatography on bacitracin-Sepharose 4B using a modification of the method of Stepanov and Rudenskaya. Bacitracin-Sepharose 4B was equilibrated with 0.04M Tris/HCL, pH 7.9. Enzyme solution in 0.04M Tris/HCL pH 7.9 was applied to the column and the column was washed with the same buffer to remove all unbound protein. In the case of the recombinant enzyme the enzyme required heat activation before being applied onto the column. It was heated at 50° C. for 20 min in 0.04M Tris/HCL pH 7.9, followed by 10 min at 60° C.). The protease was then eluted from the column with 25% (v/v) propan-2-ol in 0.04M Tris/HCL pH 7.9, containing 1M NaCl at a flow rate of 0.5 ml/min. The eluate was then dialysed.

Protease Assay

In the standard protease assay, activity was determined by the addition of 50 µl enzyme to 50 µl bovine serum albumin (BSA) (1%, w/v) in 0.1M CAPS buffer, pH 10.0 and incubated for 30 min at 40° C. or 60° C. (where indicated). The reaction was then stopped by the addition of 200 µl 5% (w/v) trichloroacetic acid (TCA). After 10 min the precipitate was centrifuged at 3,000 g for 10 min. Total protein concentration in the supernatant was measured using the bicinchoninic acid (BCA) protein assay kit (Sigma) or Bradford assay. A unit of activity is defined as the amount of enzyme releasing 1 mg TCA soluble protein fragments from BSA in 30 min at 40° C. or 60° C.

Western Blotting

For PrP$^{Sc}$ analysis, lysates prepared to 50 µg were digested with 16 µg of proteinase K (pK)/mg of protein at 37° C. for 15 min, or as indicated, the reaction was then stopped with 1 mM pefabloc. Samples in loading buffer were boiled for 5 min and loaded onto 12% SDS-PAGE and analysed by western blotting employing standard techniques. For PrP$^C$ and or total PrP analysis, lysates were not pK digested. PrP was detected by incubating immunoblots with the antibodies indicated in the text followed by a horseradish peroxidase secondary antibody and developed by enhanced chemiluminescence (ECL).

Mice and RML Intracerebral Inoculations

CD1 male mice used and at 5-6 weeks of age they were injected with 20 µl of 1% RML brain homogenate intracerebrally into the left parietal region. Initial 10% brain homogenates was prepared in 0.32M sucrose, and was then diluted in 1% PBS containing 2% fetal bovine serum. Inoculated mice were monitored closely for clinical signs of mouse prion disease and were sacrificed at the point of development of neurological disease.

Degradation of Prion in Brain Homogenate

Brain homogenate (10%, w/v), from TgA20 mice infected with the RML scrapie strain was prepared by passing the brain successively through 18, 20 and 23 gauge needles in PBS until free flowing. 50 µg infected brain homogenate was resupsended in 0.1M HEPES buffer pH7.0 (B), or in 0.1M HEPES buffer pH7.0 containing the units of enzyme (E) indicated or boiled heat inactivate enzyme (BE). BE and E samples were incubated for 15 min, E treated samples were incubated for the time indicated, at 22° C. Samples were then solvent precipitated, pellets were resuspended in LB buffer (0.5% (v/v) Triton X-100, 0.5% (w/v) sodium deoxycholate, 150 mM NaCl and 50 mM Tris-HCl (pH 7.5), 1pg/ml pepstatin, 1pg/ml leupeptin, 2 mM EDTA) and left on ice for 20 min. Where brain homogenate was pK (+) digested the homogenate was treated with 16 µg of proteinase K (pK)/mg protein for 30 min at 37° C. Samples were then analysed for PrP levels.

Cloning of the Prion Degrading Protease of Thermoactinomycete p 16.

The purified serine protease of *Thermoactinomyces* sp 16 was analysed by Mass spectrometry, this identified the protease as a Thermitase. Jorgensen et al (12) recently published work (Jorgensen et al., (2013) *Protein expression and purification* 92:148-155) on the recombinant expression of an Actinomycete *Laceyella sacchari* Thermitase; their work identified that their full protease gene included a signal peptide, a pro peptide domain, followed by the mature protease domain. The propeptide domain enables correct folding of the mature protease, but is naturally removed by the host on secretion of the mature enzyme. Its removal is essential for enzyme activity as it inhibits the enzyme when bound. To isolate the protease primers were designed for the complete *Thermoactinomyces* sp 16 Thermitase gene (Table 6), from which the gene was isolated as a 1.16 kb PCR fragment. The gene was DNA sequenced (Table 6) and the translated protein sequence was identified to be composed of three distinct regions a 25 amino acid signal peptide, an 83 amino acid propeptide and the mature protease region of 279 amino acid (Table 7).

TABLE 6

```
Signal peptide: 1-75
                                          [SEQ ID NO: 10]
atgaagaaac gcgtttccct catcgcttcc ttcgttttga
tggcaagcgc cgccctgcct tccgccattt tcgct Propeptide: 76-324
                                          [SEQ ID NO: 11]
gagga agtagatagc caagcgggta aactctatgc
tccagggcaa gtcgtggtga aatacaaaga caatgcttcg
gccagcgccg tcaaatctgc ccgcgccaaa gccaacggta
cagtcatgga gaaaacaac aagctcggct ttgaagtggt
caaagtgaaa ggctctgtgg aagcgaccat cgaaaagctg
aaaaaagacc ccaacgtgga atatgctgaa cccaactact
atctccacgc tacc
```

TABLE 6-continued

Mature protease: 325-1161
[SEQ ID NO: 12]
```
tacaca cctaacgatc cttacttcag ctcccgccaa
tacggcccac aaaaaatcca agcgccgcag gcatgggaca
tcgctgaagg ctccggcgtg aaaatcgcca tcgtcgacac
cggggtgcaa tccaaccatc ccgacttggc cggtaaagta
gtgggcggtt gggacttcgt tgacaacgac tccactccgc
aagatggcaa cggccacggt acacactgcg ctggtatcgc
cgcagcagtg accaacaaca gcaccgggat cgctggtact
gccccgaaag cgtcaatcct cgctgtgcgc gtgctggaca
acagcggtag cggcacctgg actgctgtcg ccaacggtat
cacctatgct gcagaccaag gcgctaaagt catcagcttg
agcttgggcg gcaccgttgg taactccggt ctgcaacaag
ctgtcgacta cgcttggaac aaaggttccg ttgtcgtggc
cgcggctggt aacgccggca acaccgctcc taactatccc
gcttactatt ccaacgccat cgcggtagct tctactgacc
aaaatgacaa caaatcctcc ttctccactt acggttcctg
ggtagatgta gctgctcctg gttccagcat ctattccacc
tacccgacca gcacctacgc ttccttgagc ggtacctcca
tggctactcc tcacgtagct ggtgtggctg gactcttggc
ttcccaaggc cgtagcgctt ccaatatccg cgccgccatt
gaaaacaccg ccgacaaaat cagcggcact ggcacctact
gggccaaagg acgcgtcaac gcttacaaag ctgttcagta
ctaa
```

TABLE 7

Signal peptide:
[SEQ ID NO: 13]
M K K R V S L I A S F V L M A S A A L P
S A I F A Propeptide:
[SEQ ID NO: 14]
E E V D S Q A G K L Y A P G Q V V V K Y
K D N A S A S A V K S A R A K A N G T V
M E K N N K L G F E V V K V K G S V E A
T I E K L K K D P N V E Y A E P N Y Y L
H A T Mature protease:
[SEQ ID NO: 15]
Y T P N D P Y F S S R Q Y G P Q K I Q A
P Q A W D I A E G S G V K I A I V D T G
V Q S N H P D L A G K V V G G W D F V D
N D S T P Q D G N G H G T H C A G I A A
A V T N N S T G I A G T A P K A S I L A
V R V L D N S G S G T W T A V A N G I T
Y A A D Q G A K V I S L S L G G T V G N
S G L Q Q A V D Y A W N K G S V V V A A
A G N A G N T A P N Y P A Y Y S N A I A
V A S T D Q N D N K S S F S T Y G S W V
D V A A P G S S I Y S T Y P T S T Y A S
L S G T S M A T P H V A G V A G L L A S
Q G R S A S N I R A A I E N T A D K I S
G T G T Y W A K G R V N A Y K A V Q Y Using the GenBank BLAST P programme the pro-peptide was identified as possessing an 19 inhibitor (13) with complete homology to that of the *L. sacchari* Thermitase (12). The mature protease aligns with the Peptidase S8 family domain in Thermitase-like proteins; it differs from its most closely related Thermitase of *L. sacchari* by two amino acids as indicated in Table 7.

Recombinant Production of the Thermoactinomycete Sp 16 Thermitase

The protease gene lacking its signal peptide was cloned into the pAMJ2008 vector system, the PCR inserts including the cloning junctions were confirmed by DNA sequencing. The pAMJ2008 vector employs the *L. lactis* signal peptide SP310mut2 which facilitates secretion of the protease to the eternal milieu, as the signal peptide is cleaved during translocation. The expression strain chosen was the *L. lactis* strain MG1363 which itself lacks any host protease secretion. The Thermitase was released as an inactive pro-enzyme which required release of the prodomain, this was accomplished by heat treatment. The protease was produced in batch culture and was purified by ammonium sulphate (0-60%) fractionation, followed by affinity chromatography on bacitracin-Sepharose 4B (Table 8). The non-recombinant Thermoactinomycete sp 16 Thermitase was produced as described previously.

TABLE 8

| Purification Step | Specific activity (units/mg protein) | Purification (X-fold) | Recovery (%) |
| --- | --- | --- | --- |
| Cell free supernatant | 0.125 | 1.00 | 100 |
| (NH$_4$)$_2$SO$_4$ (0-60%) fractionation | 2.26 | 18.08 | 86.13 |
| Bacitricin-Sepharose 4B | 12.86 | 102.88 | 31.35 |

(*L. lactis* strain 16 was grown for 8 h at 30° C., pH6.5 and 200 rpm. Cells were then removed from the culture by centrifugation at 10,000 g for 15 min 4° C. The supernatant was then purified by (NH$_4$)$_2$SO$_4$ (0-60%) fractionation, heat treatment followed by affinity chromatography on Bacitricin-Sepharose 4B).

Degradation of PrP$^{Sc}$ from Infected Brain Homogenate by the Thermoactinomycete Sp 16 Thermitase.

It was decided to recombinantly produce the Thermitase of the Thermoactinomycete sp 16 and assess whether it would maintain its ability to degrade PrP$^{Sc}$ under mild conditions at 22° C. and at pH 7.0 after 15 min. Prion degradation was tested with the scrapie strain RML. 50 µg RML brain homogenate was exposed to 0.5 units/ml of recombinant Thermitase (RE) and of the original enzyme (E) at 22° C. for 15 min, this was found to be sufficient to remove all traces of the RML prion strain as detected by western blot (as shown in FIG. 8, lane 6 and 7).

Results of Cloning of the *Thermoactinomyces* sp 16 Protease

The Thermitase was successfully expressed in the *L. lactis* strain MG1363 under the control of the vector system pAMJ2008. This vector has previously been reported to successfully allow for the expression of the Thermitase of *L. sacchari* in *L. lacti*. The vector's SP310mut2 facilitated the external secretion of our protease which then required heat to enable activation due to its prodomain. As mentioned the Thermoactinomycete sp16 Thermitase is composed of a pro-domain, these domains are known for their significance in the correct folding of specific active mature proteases, but they also render the protease inactive whilst attached. In the case of the prodomain of subtilisin it inhibits activity through the binding of its prodomain C-terminus to the mature enzymes active site much like a substrate and can be released auto-catalytically under appropriate conditions. Like other Thermitases heating facilitated activation and release of the mature Thermoactinomycete sp16 Thermitase.

The recombinant Thermitase 16 was tested for its ability to degrade the RML prion, and like the original enzyme it degraded the prion within 15 min at 22° C. and at pH 7.0. Thus far this protease is believed to be the first to degrade prion material under such mild conditions. The Thermitase 16 represents the first enzyme capable of degrading the prion under true environmental conditions. The nature of the Thermitase enables for diversity in the cleavage sites of its substrate. They belong to the subtilases, and possess good substrate diversity this characteristic has been seen as beneficial in the degradation of proteins in to smaller peptides than potentially seen with subtilisin itself. This diversity in the degradation profile of this group of proteases is most likely the reason why Thermitase 16 can overcome the complex protein β-sheet structure of PrP$^{Sc}$ which has challenged the heretofore methods employed to decontaminate prion material.

Effect of pH on Protease Activity of the Original and Recombinant Protease 16

The original and recombinant proteinase 16 were assayed using BSA (1%, w/v) as substrate in 0.1M Universal buffer at the pH values indicated for 30 min at 40 C. FIG. 9 shows that there was little difference in activity levels between both proteases at the same pHs.

Cloning of the *Thermoactinomyces* sp 10 Protease

It was decided to clone and analyse protease 10 (Thermitase 10) which had also been found to degrade prions under mild conditions at pH 7.0 and 22° C. The protease sequence differs significantly to those published, also to the sequence of protease 16 which is described above. Similar methods were employed as for the cloning and analysis of protease 16.

Cloning of the *Thermoactinomyces* sp 10 Protease

The *Thermoactinomyces* sp 10 enzyme responsible for the degradation of PrP$^{Sc}$ was cloned using the primers employed for *Thermoactinomyces* sp 16. Cloning was carried out as preformed for *Thermoactinomyces* sp 16. The gene encoding Thermitase 10 was PCR amplified using Thermitase FL-Sapl F and Thermitase FL-Xhol R (as detailed in table 5) and its product was ligated to pAMJ2008 and transformed into *Escherichia coli* DH5α.

The full sequence was obtained through DNA sequencing. The Thermitase gene lacking the N-terminal signal peptide was generated by PCR amplification of the gene using the primer combination Thermitase ΔN-sapl F and Thermitase FL-Xhol R (as detailed in Table 5). This product was cloned into pAMJ2008, and transformed into *E. coli* DH5α in which the plasmid was developed. The entire plasmid containing the Thermitase gene lacking its signal peptide was subsequently cloned into *L. lactis* strain MG1363 generating *L. lactis* strain 10. The final sequence was confirmed by DNA sequencing.

Recombinant Protease Production

The recombinant production of the protease of Thermoactinomycete sp. 10 was produced in the same manner as that of Thermoactinomycete sp. 16.

Cloning of the Prion Degrading Protease of Thermoactinomycete Sp 10

The Thermitase of *Thermoactinomyces* sp 10 was cloned using the same cloning strategy used for *Thermoactinomyces* sp 16. The gene was DNA sequenced and is detailed in Table 9 and the translated protein sequence was identified to be composed of three distinct regions a 25 amino acid signal peptide, an 83 amino acid propeptide and the mature protease region of 279 amino acid and is detailed in Table 10, as per Thermoactinomycete 16.

TABLE 9

Signal peptide: 1-75
[SEQ ID NO: 15]
```
atgaagaaac gcgtttcct catcgcttcc ttcgttttga
tggccagcgc cgccctgcct tccgccattt tcgca
```

Propeptide: 76-324
[SEQ ID NO: 16]
```
gagga agtagatagc caagcgggta aactctacgc
ccccgggcaa gttgtggtga aatacaaaga caatgcttcg
gccagcgctg tcaaatctgc ccgcgccaaa gccaacggta
```

TABLE 9-continued

```
cagtcatgga gaaaaacaac aagctcggct tcgaagtggt
caaagtgaaa ggctctgtgg aagcgaccat cgaaaagctg
aaaaaagacc ccaacgtgga atatgctgag cccaactact
atctccacgc ttcc
```

Mature protease: 325-1164
[SEQ ID NO: 17]
```
tacacg cctaacgatc cttacttcag cacccgccaa
tacggcccac aaaaaatcca agcgccacaa gcatgggaca
tcactgaagg ctccggcgcg aagatcgcca tcgtcgacac
cggggtacaa tccaaccatc ccgacttggc cggtaaagta
gtgggcggtt gggacttcgt tgacaacgac tccacgccac
aagatggcaa cggccacggt acccactgcg ctggtatcgc
cgcagcagtg accaacaaca gcaccgggat cgctggtact
gctccaaaag cgtcgatcct cgctgtgcgc gtgctggaca
acagtggtag cggcacctgg actgctgtcg ccaacggtat
cacctatgcc gcagaccaag gtgctgacgt catcagcttg
agcttgggcg gcaccgtcgg taactccggt ctgcaacaag
ctgtcaacta cgcttggaac aaaggttctg ttgtcgtggc
cgcagctggt aacgccggca acaccgctcc tcactatcct
gcatactatt ccaacgccat cgcggtagct tctactgacc
aaaatgacaa caaatcctcc ttctccactt acggttcctg
ggtagatgta gccgctcctg gttccagcat ctatgctact
tatccgacca gcacctacgc ttccttgagc ggtacctcca
tggctactcc ccatgtggct ggagtggctg gactcctggc
ttcccaaggc cgtagtgctt ccaacatccg cgccgctatt
gaaaacaccg ccgacaaaat cagcggcacc ggctcctact
gggccaaagg gcgcgtcaac gcttacaaag ctgttcagta
ctaa
```

TABLE 10

Signal peptide:
[SEQ ID NO: 18]
MKKRVSLIASFVLMASAALPSAIFA

Propeptide:
[SEQ ID NO: 19]
EEVDSQAGKLYAPGQVVVKYKDNASASAVKSARAKANGTVME
KNNKLGFEVVKVKGSVEATIEKLKKDPNVEYAEPNYYLHAS Mature protease:
[SEQ ID NO: 4]
YTPNDPYFSTRQYGPQKIQAPQAWDITEGSGAKIAIVDTGVQ
SNHPDLAGKVVGGWDFVDNDSTPQDGNGHGTHCAGIAAAVTN
NSTGIAGTAPKASILAVRVLDNSGSGTWTAVANGITYAADQG
ADVISLSLGGTVGNSGLQQAVNYAWNKGSVVVAAAGNAGNTA
PHYPAYYSNAIAVASTDQNDNKSSFSTYGSWVDVAAPGSSIY
ATYPTSTYASLSGTSMATPHVAGVAGLLASQGRSASNIRAAI
ENTADKISGTGSYWAKGRVNAYKAVQY*

The protease gene sequence differed from both the Thermitase of the published sequence of *L. sacchari* and that of *Thermoactinomyces* sp 16. The bases that differ from both are highlighted in yellow, and those highlighted in red are specific differences between the gene of protease 10 and that of *L. sacchari*. As with the Thermitase of *Thermoactinomyces* sp 16, Thermitase 10 aligns with the Peptidase S8 family domain in Thermitase-like proteins. It differs from its most closely related published Thermitase of *L. sacchari* by 12 amino acids. From Thermitase 16 it differs by 9 amino acids, one of which is located in the prodomain of the protease (Table 10).

CONCLUSIONS

The Thermitase of *Thermoactinomyces* sp. 10 was expressed in the *L. lactis* strain MG1363 under the control of the vector system pAMJ2008, as per the *Thermoactinomyces* sp 16 Thermitase. Like the *Thermoactinomyces* sp16 Thermitase, Thermitase 10 has a pro-domain, a domain that is known for its significance in the correct folding of specific active mature proteases, it also renders the protease inactive whilst attached. This applied to Thermitase 10, and the protease required heating to enable activation of the mature protease.

As shown FIG. 10, alignment between the mature amino acid sequences of protease 16 and protease 10 provides 97% identity and 98% positives. As shown in FIG. 11, alignment between the complete signal, pro-domain and mature amino acid sequences of protease 16 and protease 10 provides a 98% identities and 99% positives. As shown in FIG. 12, alignment between the amino acid sequences of protease 16 and a thermitase precursor (*Laceyella sacchari*) provides a 99% identity and 99% positives. As shown in FIG. 13, alignment between the amino acid sequences of protease 10 and a thermitase precursor (*Laceyella sacchari* provides 97% identity and 98% positives). As shown in FIG. 14, alignment between the mature gene sequences of protease 16 and protease 10 provides 95% identity. As shown in FIG. 15, alignment between the gene sequences of protease 16 and protease 10 provides 96% identity. As shown in FIG. 16, alignment between the gene sequences of protease 16 and a thermitase precursor (*Laceyella sacchari*) provides 99% identity. Lastly, FIG. 17 shows alignment between the gene sequences of protease 10 and a thermitase precursor (*Laceyella sacchari*) providing 95% identity.

The forgoing embodiments are not intended to limit the scope of the protection afforded by the claims, but rather to describe examples of how the invention may be put into practice.

Indications of Deposited Biological Material

A deposition of biological material was made to National Collections of Industrial and Marine Bacteria Limited (NCIMB) for the purposes of filing one or more patent applications. The National Collections of Industrial and Marine Bacteria Limited (NCIMB) is a recognised International Depository Authority (IDA) under the Budapest Treaty and the deposition of biological material was made on the same terms as those laid down in the Treaty. The deposit has been assigned a number along with the prefix "NCIMB".

The deposited biological referred to in this application is as follows:

| | |
|---|---|
| Name: | National Collections of Industrial and Marine Bacteria Limited (NCIMB) |
| Depositor: | University College Dublin |
| Address: | Ferguson Building |
| | Craibstone Estate, |
| | Bucksburn, |
| | Aberdeen, |
| | AB21 9YA, |
| | Scotland, |
| | UK |
| Date: | 18 Aug. 2010 |
| Accession Number: | NCIMB 41754 |
| Description: | *Thermoactinomyces* sp 16 strain (initially referenced as *Streptomyces* sp strain No. 16) |

The invention claimed is:

1. A disinfectant composition for degrading a PrP$^{sc}$ prion or PrP$^{sc}$ prion material on medical equipment or in the environment, the disinfectant composition comprising a Thermitase and a buffer, wherein the Thermitase is present in an effective amount to degrade the PrP$^{sc}$ prion or PrP$^{sc}$ prion material to an undetectable level when measured according to a western blot analysis.

2. The disinfectant composition as claimed in claim 1, wherein the Thermitase has the amino acid sequence of SEQ ID NO: 1 and/or SEQ ID NO: 4, or a sequence having 95% or more homology thereof.

3. The disinfectant composition as claimed in claim 1, wherein the Thermitase has the amino acid sequence of SEQ ID NO: 1 and/or SEQ ID NO: 4, or an amino acid sequence or amino acid sequences having 98% or more homology thereof.

4. The disinfectant composition as claimed in claim 1, wherein the composition has a pH in the range of 6 to 13.

5. The disinfectant composition as claimed in claim 1, wherein the Thermitase is active in the range of 10° C. to 65° C.

6. The disinfectant composition as claimed in claim 1, wherein the composition is formulated in the form of a solution or is formulated so as to easily form a solution if desired.

7. The disinfectant composition as claimed in claim 6, wherein the solution is an aqueous solution.

8. The disinfectant composition as claimed in claim 1, wherein the Thermitase is in a lyophilised form.

9. The disinfectant composition as claimed in claim 1, wherein the composition comprises two or more Thermitases.

10. The disinfectant composition as claimed in claim 1, wherein the composition is in the form of a ready-made solution or spray.

11. A protease having the amino acid sequence of: SEQ ID NO: 1, SEQ ID NO: 2, SEQ ID NO: 4, or SEQ ID NO: 5.

12. The protease as claimed in claim 11, for use in degrading prions or prion material.

13. A method for prion disinfection, the method comprising contacting a substrate containing and/or coated with prion material with a disinfectant composition according to claim 1.

14. A method as claimed in claim 13, wherein the method is conducted under conditions effective to enable the activation or activity of the Thermitase to degrade prion material.

15. A method as claimed in claim 13, wherein the method is conducted in the range of about 10° C. to 65° C. and/or a pH in the range of about 6 to 13.

16. A method as claimed in claim 13, wherein the Thermitase comprises the amino acid sequence of SEQ ID No. 1, SEQ ID No. 4, or an amino acid sequence having 95% or more homology thereof.

17. A kit of parts for prion disinfection, comprising:
   a) a Thermitase having the amino acid sequence of: SEQ ID NO: 1 and/or SEQ ID NO: 4, or a sequence having 95% or more homology thereof; and
   b) a buffer solution having a pH in the range of 6 to 13.

* * * * *

SEQUENCE LISTING

```
<160> NUMBER OF SEQ ID NOS: 22

<210> SEQ ID NO 1
<211> LENGTH: 279
<212> TYPE: PRT
<213> ORGANISM: Thermoactinomyces sp. 16

<400> SEQUENCE: 1

Tyr Thr Pro Asn Asp Pro Tyr Phe Ser Ser Arg Gln Tyr Gly Pro Gln
1               5                   10                  15

Lys Ile Gln Ala Pro Gln Ala Trp Asp Ile Ala Glu Gly Ser Gly Val
            20                  25                  30

Lys Ile Ala Ile Val Asp Thr Gly Val Gln Ser Asn His Pro Asp Leu
        35                  40                  45

Ala Gly Lys Val Val Gly Gly Trp Asp Phe Val Asp Asn Asp Ser Thr
    50                  55                  60

Pro Gln Asp Gly Asn Gly His Gly Thr His Cys Ala Gly Ile Ala Ala
65                  70                  75                  80

Ala Val Thr Asn Asn Ser Thr Gly Ile Ala Gly Thr Ala Pro Lys Ala
                85                  90                  95

Ser Ile Leu Ala Val Arg Val Leu Asp Asn Ser Gly Ser Gly Thr Trp
            100                 105                 110

Thr Ala Val Ala Asn Gly Ile Thr Tyr Ala Ala Asp Gln Gly Ala Lys
        115                 120                 125

Val Ile Ser Leu Ser Leu Gly Gly Thr Val Gly Asn Ser Gly Leu Gln
    130                 135                 140

Gln Ala Val Asp Tyr Ala Trp Asn Lys Gly Ser Val Val Val Ala Ala
145                 150                 155                 160

Ala Gly Asn Ala Gly Asn Thr Ala Pro Asn Tyr Pro Ala Tyr Tyr Ser
                165                 170                 175
```

```
Asn Ala Ile Ala Val Ala Ser Thr Asp Gln Asn Asp Asn Lys Ser Ser
            180                 185                 190

Phe Ser Thr Tyr Gly Ser Trp Val Asp Val Ala Ala Pro Gly Ser Ser
            195                 200                 205

Ile Tyr Ser Thr Tyr Pro Thr Ser Thr Tyr Ala Ser Leu Ser Gly Thr
            210                 215                 220

Ser Met Ala Thr Pro His Val Ala Gly Val Ala Gly Leu Leu Ala Ser
225                 230                 235                 240

Gln Gly Arg Ser Ala Ser Asn Ile Arg Ala Ala Ile Glu Asn Thr Ala
            245                 250                 255

Asp Lys Ile Ser Gly Thr Gly Thr Tyr Trp Ala Lys Gly Arg Val Asn
            260                 265                 270

Ala Tyr Lys Ala Val Gln Tyr
            275
```

<210> SEQ ID NO 2
<211> LENGTH: 387
<212> TYPE: PRT
<213> ORGANISM: Thermoactinomyces sp. 16

<400> SEQUENCE: 2

```
Met Lys Lys Arg Val Ser Leu Ile Ala Ser Phe Val Leu Met Ala Ser
1               5                   10                  15

Ala Ala Leu Pro Ser Ala Ile Phe Ala Glu Glu Val Asp Ser Gln Ala
            20                  25                  30

Gly Lys Leu Tyr Ala Pro Gly Gln Val Val Lys Tyr Lys Asp Asn
            35                  40                  45

Ala Ser Ala Ser Ala Val Lys Ser Ala Arg Ala Lys Ala Asn Gly Thr
    50                  55                  60

Val Met Glu Lys Asn Asn Lys Leu Gly Phe Glu Val Val Lys Val Lys
65                  70                  75                  80

Gly Ser Val Glu Ala Thr Ile Glu Lys Leu Lys Lys Asp Pro Asn Val
            85                  90                  95

Glu Tyr Ala Glu Pro Asn Tyr Tyr Leu His Ala Thr Tyr Thr Pro Asn
            100                 105                 110

Asp Pro Tyr Phe Ser Ser Arg Gln Tyr Gly Pro Gln Lys Ile Gln Ala
            115                 120                 125

Pro Gln Ala Trp Asp Ile Ala Glu Gly Ser Gly Val Lys Ile Ala Ile
            130                 135                 140

Val Asp Thr Gly Val Gln Ser Asn His Pro Asp Leu Ala Gly Lys Val
145                 150                 155                 160

Val Gly Gly Trp Asp Phe Val Asp Asn Asp Ser Thr Pro Gln Asp Gly
            165                 170                 175

Asn Gly His Gly Thr His Cys Ala Gly Ile Ala Ala Ala Val Thr Asn
            180                 185                 190

Asn Ser Thr Gly Ile Ala Gly Thr Ala Pro Lys Ala Ser Ile Leu Ala
            195                 200                 205

Val Arg Val Leu Asp Asn Ser Gly Ser Gly Thr Trp Thr Ala Val Ala
            210                 215                 220

Asn Gly Ile Thr Tyr Ala Ala Asp Gln Gly Ala Lys Val Ile Ser Leu
225                 230                 235                 240

Ser Leu Gly Gly Thr Val Gly Asn Ser Gly Leu Gln Gln Ala Val Asp
            245                 250                 255

Tyr Ala Trp Asn Lys Gly Ser Val Val Val Ala Ala Ala Gly Asn Ala
```

```
            260                 265                 270
Gly Asn Thr Ala Pro Asn Tyr Pro Ala Tyr Tyr Ser Asn Ala Ile Ala
        275                 280                 285

Val Ala Ser Thr Asp Gln Asn Asp Asn Lys Ser Ser Phe Ser Thr Tyr
        290                 295                 300

Gly Ser Trp Val Asp Val Ala Ala Pro Gly Ser Ser Ile Tyr Ser Thr
305                 310                 315                 320

Tyr Pro Thr Ser Thr Tyr Ala Ser Leu Ser Gly Thr Ser Met Ala Thr
                325                 330                 335

Pro His Val Ala Gly Val Ala Gly Leu Leu Ala Ser Gln Gly Arg Ser
            340                 345                 350

Ala Ser Asn Ile Arg Ala Ala Ile Glu Asn Thr Ala Asp Lys Ile Ser
        355                 360                 365

Gly Thr Gly Thr Tyr Trp Ala Lys Gly Arg Val Asn Ala Tyr Lys Ala
    370                 375                 380

Val Gln Tyr
385

<210> SEQ ID NO 3
<211> LENGTH: 840
<212> TYPE: DNA
<213> ORGANISM: Thermoactinomyces sp. 16

<400> SEQUENCE: 3
tacacaccta acgatcctta cttcagctcc cgccaatacg gcccacaaaa aatccaagcg      60
ccgcaggcat gggacatcgc tgaaggctcc ggcgtgaaaa tcgccatcgt cgacaccggg     120
gtgcaatcca accatcccga cttggccggt aaagtagtgg gcggttggga cttcgttgac     180
aacgactcca ctccgcaaga tggcaacggc acggtacac actgcgctgg tatcgccgca     240
gcagtgacca acaacagcac cgggatcgct ggtactgccc cgaaagcgtc aatcctcgct     300
gtgcgcgtgc tggacaacag cggtagcggc acctggactg ctgtcgccaa cggtatcacc     360
tatgctgcag accaaggcgc taaagtcatc agcttgagct tgggcggcac cgttggtaac     420
tccggtctgc aacaagctgt cgactacgct tggaacaaag gttccgttgt cgtggccgcg     480
gctggtaacg ccggcaacac cgctcctaac tatcccgctt actattccaa cgccatcgcg     540
gtagcttcta ctgaccaaaa tgacaacaaa tcctccttct ccacttacgg ttcctgggta     600
gatgtagctg ctcctggttc cagcatctat tccacctacc cgaccagcac ctacgcttcc     660
ttgagcggta cctccatggc tactcctcac gtagctggtg tggctggact cttggcttcc     720
caaggccgta gcgcttccaa tatccgcgcc gccattgaaa acaccgccga caaaatcagc     780
ggcactggca cctactgggc caaggacgc gtcaacgctt acaaagctgt tcagtactaa     840

<210> SEQ ID NO 4
<211> LENGTH: 279
<212> TYPE: PRT
<213> ORGANISM: Thermoactinomyces sp. 10

<400> SEQUENCE: 4

Tyr Thr Pro Asn Asp Pro Tyr Phe Ser Thr Arg Gln Tyr Gly Pro Gln
1               5                   10                  15

Lys Ile Gln Ala Pro Gln Ala Trp Asp Ile Thr Glu Gly Ser Gly Ala
            20                  25                  30

Lys Ile Ala Ile Val Asp Thr Gly Val Gln Ser Asn His Pro Asp Leu
        35                  40                  45
```

```
Ala Gly Lys Val Val Gly Gly Trp Asp Phe Val Asp Asn Asp Ser Thr
     50              55                  60
Pro Gln Asp Gly Asn Gly His Gly Thr His Cys Ala Gly Ile Ala Ala
 65                  70                  75                  80
Ala Val Thr Asn Asn Ser Thr Gly Ile Ala Gly Thr Ala Pro Lys Ala
                 85                  90                  95
Ser Ile Leu Ala Val Arg Val Leu Asp Asn Ser Gly Ser Gly Thr Trp
                100                 105                 110
Thr Ala Val Ala Asn Gly Ile Thr Tyr Ala Ala Asp Gln Gly Ala Asp
                115                 120                 125
Val Ile Ser Leu Ser Leu Gly Gly Thr Val Gly Asn Ser Gly Leu Gln
130                 135                 140
Gln Ala Val Asn Tyr Ala Trp Asn Lys Gly Ser Val Val Ala Ala
145                 150                 155                 160
Ala Gly Asn Ala Gly Asn Thr Ala Pro His Tyr Pro Ala Tyr Tyr Ser
                165                 170                 175
Asn Ala Ile Ala Val Ala Ser Thr Asp Gln Asn Asp Asn Lys Ser Ser
                180                 185                 190
Phe Ser Thr Tyr Gly Ser Trp Val Asp Val Ala Ala Pro Gly Ser Ser
                195                 200                 205
Ile Tyr Ala Thr Tyr Pro Thr Ser Thr Tyr Ala Ser Leu Ser Gly Thr
                210                 215                 220
Ser Met Ala Thr Pro His Val Ala Gly Val Ala Gly Leu Leu Ala Ser
225                 230                 235                 240
Gln Gly Arg Ser Ala Ser Asn Ile Arg Ala Ala Ile Glu Asn Thr Ala
                245                 250                 255
Asp Lys Ile Ser Gly Thr Gly Ser Tyr Trp Ala Lys Gly Arg Val Asn
                260                 265                 270
Ala Tyr Lys Ala Val Gln Tyr
                275

<210> SEQ ID NO 5
<211> LENGTH: 387
<212> TYPE: PRT
<213> ORGANISM: Thermoactinomyces sp. 10

<400> SEQUENCE: 5

Met Lys Lys Arg Val Ser Leu Ile Ala Ser Phe Val Leu Met Ala Ser
 1               5                  10                  15
Ala Ala Leu Pro Ser Ala Ile Phe Ala Glu Glu Val Asp Ser Gln Ala
                 20                  25                  30
Gly Lys Leu Tyr Ala Pro Gly Gln Val Val Lys Tyr Lys Asp Asn
                 35                  40                  45
Ala Ser Ala Ser Ala Val Lys Ser Ala Arg Ala Lys Ala Asn Gly Thr
     50                  55                  60
Val Met Glu Lys Asn Asn Lys Leu Gly Phe Glu Val Val Lys Val Lys
 65                  70                  75                  80
Gly Ser Val Glu Ala Thr Ile Glu Lys Leu Lys Lys Asp Pro Asn Val
                 85                  90                  95
Glu Tyr Ala Glu Pro Asn Tyr Tyr Leu His Ala Ser Thr Pro Asn
                100                 105                 110
Asp Pro Tyr Phe Ser Thr Arg Gln Tyr Gly Pro Gln Lys Ile Gln Ala
                115                 120                 125
Pro Gln Ala Trp Asp Ile Thr Glu Gly Ser Gly Ala Lys Ile Ala Ile
130                 135                 140
```

```
Val Asp Thr Gly Val Gln Ser Asn His Pro Asp Leu Ala Gly Lys Val
145                 150                 155                 160

Val Gly Gly Trp Asp Phe Val Asp Asn Asp Ser Thr Pro Gln Asp Gly
            165                 170                 175

Asn Gly His Gly Thr His Cys Ala Gly Ile Ala Ala Val Thr Asn
        180                 185                 190

Asn Ser Thr Gly Ile Ala Gly Thr Ala Pro Lys Ala Ser Ile Leu Ala
        195                 200                 205

Val Arg Val Leu Asp Asn Ser Gly Ser Gly Thr Trp Thr Ala Val Ala
210                 215                 220

Asn Gly Ile Thr Tyr Ala Ala Asp Gln Gly Ala Asp Val Ile Ser Leu
225                 230                 235                 240

Ser Leu Gly Gly Thr Val Gly Asn Ser Gly Leu Gln Gln Ala Val Asn
            245                 250                 255

Tyr Ala Trp Asn Lys Gly Ser Val Val Ala Ala Ala Gly Asn Ala
        260                 265                 270

Gly Asn Thr Ala Pro His Tyr Pro Ala Tyr Tyr Ser Asn Ala Ile Ala
        275                 280                 285

Val Ala Ser Thr Asp Gln Asn Asp Asn Lys Ser Ser Phe Ser Thr Tyr
290                 295                 300

Gly Ser Trp Val Asp Val Ala Ala Pro Gly Ser Ser Ile Tyr Ala Thr
305                 310                 315                 320

Tyr Pro Thr Ser Thr Tyr Ala Ser Leu Ser Gly Thr Ser Met Ala Thr
            325                 330                 335

Pro His Val Ala Gly Val Ala Gly Leu Leu Ala Ser Gln Gly Arg Ser
            340                 345                 350

Ala Ser Asn Ile Arg Ala Ala Ile Glu Asn Thr Ala Asp Lys Ile Ser
        355                 360                 365

Gly Thr Gly Ser Tyr Trp Ala Lys Gly Arg Val Asn Ala Tyr Lys Ala
        370                 375                 380

Val Gln Tyr
385

<210> SEQ ID NO 6
<211> LENGTH: 1164
<212> TYPE: DNA
<213> ORGANISM: Thermoactinomyces sp. 10

<400> SEQUENCE: 6
atgaagaaac gcgtttccct catcgcttcc ttcgttttga tggccagcgc cgccctgcct      60
tccgccattt tcgcagagga agtagatagc caagcgggta aactctacgc ccccgggcaa     120
gttgtggtga atacaaaga caatgcttcg gccagcgctg tcaaatctgc ccgcgccaaa      180
gccaacggta cagtcatgga gaaaacaac aagctcggct tcgaagtggt caaagtgaaa      240
ggctctgtgg aagcgaccat cgaaaagctg aaaaagacc ccaacgtgga atatgctgag      300
cccaactact atctccacgc ttcctacacg cctaacgatc cttacttcag cacccgccaa     360
tacggcccac aaaaaatcca agcgccacaa gcatgggaca tcactgaagg ctccggcgcg     420
aagatcgcca tcgtcgacac cggggtacaa tccaaccatc ccgacttggc cggtaaagta     480
gtgggcggtt gggacttcgt tgacaacgac tccacgccac aagatggcaa cggccacggt     540
acccactgcg ctggtatcgc cgcagcagtg accaacaaca gcaccgggat cgctggtact     600
gctccaaaag cgtcgatcct cgctgtgcgc gtgctggaca acagtggtag cggcacctgg     660
```

| | |
|---|---|
| actgctgtcg ccaacggtat cacctatgcc gcagaccaag gtgctgacgt catcagcttg | 720 |
| agcttgggcg gcaccgtcgg taactccggt ctgcaacaag ctgtcaacta cgcttggaac | 780 |
| aaaggttctg ttgtcgtggc cgcagctggt aacgccggca acaccgctcc tcactatcct | 840 |
| gcatactatt ccaacgccat cgcggtagct tctactgacc aaaatgacaa caaatcctcc | 900 |
| ttctccactt acggttcctg ggtagatgta gccgctcctg gttccagcat ctatgctact | 960 |
| tatccgacca gcacctacgc ttccttgagc ggtacctcca tggctactcc ccatgtggct | 1020 |
| ggagtggctg gactcctggc ttcccaaggc cgtagtgctt ccaacatccg cgccgctatt | 1080 |
| gaaaacaccg ccgacaaaat cagcggcacc ggctcctact gggccaaagg cgcgtcaac | 1140 |
| gcttacaaag ctgttcagta ctaa | 1164 |

<210> SEQ ID NO 7
<211> LENGTH: 37
<212> TYPE: DNA
<213> ORGANISM: Artificial Sequence
<220> FEATURE:
<223> OTHER INFORMATION: Thermitase FL-SapI F Primer

<400> SEQUENCE: 7

| | |
|---|---|
| ctcgatgctc ttccgcaatg aagaaacgcg tttccct | 37 |

<210> SEQ ID NO 8
<211> LENGTH: 31
<212> TYPE: DNA
<213> ORGANISM: Artificial Sequence
<220> FEATURE:
<223> OTHER INFORMATION: Thermitase FL-XhoI R Primer

<400> SEQUENCE: 8

| | |
|---|---|
| ctcgagttag tactgaacag ctttgtaagc g | 31 |

<210> SEQ ID NO 9
<211> LENGTH: 39
<212> TYPE: DNA
<213> ORGANISM: Artificial Sequence
<220> FEATURE:
<223> OTHER INFORMATION: Thermitase Delta N-sapI Primer

<400> SEQUENCE: 9

| | |
|---|---|
| ctcgatgctc ttccgcagag gaagtagata gccaagcgg | 39 |

<210> SEQ ID NO 10
<211> LENGTH: 75
<212> TYPE: DNA
<213> ORGANISM: Thermoactinomyces sp. 16

<400> SEQUENCE: 10

| | |
|---|---|
| atgaagaaac gcgtttccct catcgcttcc ttcgttttga tggcaagcgc cgccctgcct | 60 |
| tccgccattt tcgct | 75 |

<210> SEQ ID NO 11
<211> LENGTH: 249
<212> TYPE: DNA
<213> ORGANISM: Thermoactinomyces sp. 16

<400> SEQUENCE: 11

| | |
|---|---|
| gaggaagtag atagccaagc gggtaaactc tatgctccag gcaagtcgt ggtgaaatac | 60 |
| aaagacaatg cttcggccag cgccgtcaaa tctgcccgcg ccaaagccaa cggtacagtc | 120 |
| atggagaaaa acaacaagct cggctttgaa gtggtcaaag tgaaaggctc tgtggaagcg | 180 |

```
accatcgaaa agctgaaaaa agaccccaac gtggaatatg ctgaacccaa ctactatctc    240
cacgctacc                                                            249

<210> SEQ ID NO 12
<211> LENGTH: 547
<212> TYPE: DNA
<213> ORGANISM: Thermoactinomyces sp. 16

<400> SEQUENCE: 12
tacacaccta acgatcctta cttcagctcc cgccaatacg gcccacaaaa aatccaagcg     60
ccgcaggcat gggacatcgc tgaaggctcc ggcgtgaaaa tcgccatcgt cgacaccggg    120
gtgcaatcca accatcccga cttggccggt aaagtagtgg gcggttggga cttcgttgac    180
aacgactcca ctccgcaaga tggcaacggc acggtacac actgcgctgg tatcgccgca    240
gcagtgacca caacagcac cgggatcgct ggtactgccc cgaaagcgtc aatcctcgct    300
gtgcgcgtgc tggacaacag cggtagcggc acctggactg ctgtcgccaa cggtatcacc    360
tatgctgcag accaaggcgc taaagtcatc agcttgagct tgggcggcac cgttggtaac    420
tccggtctgc aacaagctgt cgactacgct tggaacaaag gttccgttgt cgtggccgcg    480
gctggtaacg ccggcaacac cgctcctaac tatcccgctt actattccaa cgccatcgcg    540
gtagctt                                                              547

<210> SEQ ID NO 13
<211> LENGTH: 25
<212> TYPE: PRT
<213> ORGANISM: Thermoactinomyces sp. 16

<400> SEQUENCE: 13

Met Lys Lys Arg Val Ser Leu Ile Ala Ser Phe Val Leu Met Ala Ser
1               5                   10                  15

Ala Ala Leu Pro Ser Ala Ile Phe Ala
            20                  25

<210> SEQ ID NO 14
<211> LENGTH: 83
<212> TYPE: PRT
<213> ORGANISM: Thermoactinomyces sp. 16

<400> SEQUENCE: 14

Glu Glu Val Asp Ser Gln Ala Gly Lys Leu Tyr Ala Pro Gly Gln Val
1               5                   10                  15

Val Val Lys Tyr Lys Asp Asn Ala Ser Ala Val Lys Ser Ala
            20                  25                  30

Arg Ala Lys Ala Asn Gly Thr Val Met Glu Lys Asn Asn Lys Leu Gly
            35                  40                  45

Phe Glu Val Val Lys Val Lys Gly Ser Val Glu Ala Thr Ile Glu Lys
        50                  55                  60

Leu Lys Lys Asp Pro Asn Val Glu Tyr Ala Glu Pro Asn Tyr Tyr Leu
65                  70                  75                  80

His Ala Thr

<210> SEQ ID NO 15
<211> LENGTH: 75
<212> TYPE: DNA
<213> ORGANISM: Thermoactinomyces sp. 10

<400> SEQUENCE: 15
```

```
atgaagaaac gcgtttccct catcgcttcc ttcgttttga tggccagcgc cgccctgcct    60
tccgccattt tcgca                                                     75
```

<210> SEQ ID NO 16
<211> LENGTH: 249
<212> TYPE: DNA
<213> ORGANISM: Thermoactinomyces sp. 10

<400> SEQUENCE: 16

```
gaggaagtag atagccaagc gggtaaactc tacgcccccg gcaagttgt ggtgaaatac     60 aaagacaatg cttcggccag cgctgtcaaa tctgcccgcg ccaaagccaa cggtacagtc   120
atggagaaaa acaacaagct cggcttcgaa gtggtcaaag tgaaaggctc tgtggaagcg   180
accatcgaaa agctgaaaaa agaccccaac gtggaatatg ctgagcccaa ctactatctc   240
cacgcttcc                                                           249
```

<210> SEQ ID NO 17
<211> LENGTH: 840
<212> TYPE: DNA
<213> ORGANISM: Thermoactinomyces sp. 10

<400> SEQUENCE: 17

```
tacacgccta acgatcctta cttcagcacc cgccaatacg gcccacaaaa aatccaagcg    60
ccacaagcat gggacatcac tgaaggctcc ggcgcgaaga tcgccatcgt cgacaccggg   120
gtacaatcca accatcccga cttggccggt aaagtagtgg gcggttggga cttcgttgac   180
aacgactcca cgccacaaga tggcaacggc cacggtaccc actgcgctgg tatcgccgca   240
gcagtgacca acaacagcac cgggatcgct ggtactgctc caaaagcgtc gatcctcgct   300
gtgcgcgtgc tggacaacag tggtagcggc acctggactg ctgtcgccaa cggtatcacc   360
tatgccgcag accaaggtgc tgacgtcatc agcttgagct gggcggcac cgtcggtaac   420 tccggtctgc aacaagctgt caactacgct tggaacaaag gttctgttgt cgtggccgca   480
gctggtaacg ccggcaacac cgctcctcac tatcctgcat actattccaa cgccatcgcg   540
gtagcttcta ctgaccaaaa tgacaacaaa tcctccttct ccacttacgg ttcctgggta   600
gatgtagccg ctcctggttc cagcatctat gctacttatc cgaccagcac ctacgcttcc   660
ttgagcggta cctccatggc tactcccat gtggctggag tggctggact cctggcttcc   720
caaggccgta gtgcttccaa catccgcgcc gctattgaaa acaccgccga caaaatcagc   780
ggcaccggct cctactgggc caagggcgc gtcaacgctt acaaagctgt tcagtactaa   840
```

<210> SEQ ID NO 18
<211> LENGTH: 25
<212> TYPE: PRT
<213> ORGANISM: Thermoactinomyces sp. 10

<400> SEQUENCE: 18

```
Met Lys Lys Arg Val Ser Leu Ile Ala Ser Phe Val Leu Met Ala Ser
1               5                   10                  15

Ala Ala Leu Pro Ser Ala Ile Phe Ala
            20                  25
```

<210> SEQ ID NO 19
<211> LENGTH: 83
<212> TYPE: PRT
<213> ORGANISM: Thermoactinomyces sp. 10

<400> SEQUENCE: 19

Glu Glu Val Asp Ser Gln Ala Gly Lys Leu Tyr Ala Pro Gly Gln Val
1               5                   10                  15

Val Val Lys Tyr Lys Asp Asn Ala Ser Ala Val Lys Ser Ala
            20                  25                  30

Arg Ala Lys Ala Asn Gly Thr Val Met Glu Lys Asn Lys Leu Gly
            35                  40                  45

Phe Glu Val Val Lys Val Lys Gly Ser Val Glu Ala Thr Ile Glu Lys
    50                  55                  60

Leu Lys Lys Asp Pro Asn Val Glu Tyr Ala Glu Pro Asn Tyr Tyr Leu
65                  70                  75                  80

His Ala Ser

<210> SEQ ID NO 20
<211> LENGTH: 387
<212> TYPE: PRT
<213> ORGANISM: Laceyella sacchari

<400> SEQUENCE: 20

Met Lys Lys Arg Val Ser Leu Ile Ala Ser Phe Val Leu Met Ala Ser
1               5                   10                  15

Ala Ala Leu Pro Ser Ala Ile Phe Ala Glu Glu Val Asp Ser Gln Ala
            20                  25                  30

Gly Lys Leu Tyr Ala Pro Gly Gln Val Val Lys Tyr Lys Asp Asn
            35                  40                  45

Ala Ser Ala Ser Ala Val Lys Ser Ala Arg Ala Lys Ala Asn Gly Thr
    50                  55                  60

Val Met Glu Lys Asn Asn Lys Leu Gly Phe Glu Val Val Lys Val Lys
65                  70                  75                  80

Gly Ser Val Glu Ala Thr Ile Glu Lys Leu Lys Lys Asp Pro Asn Val
                85                  90                  95

Glu Tyr Ala Glu Pro Asn Tyr Tyr Leu His Ala Thr Tyr Thr Pro Asn
            100                 105                 110

Asp Pro Tyr Phe Ser Ser Arg Gln Tyr Gly Pro Gln Lys Ile Gln Ala
        115                 120                 125

Pro Gln Ala Trp Asp Ile Ala Glu Gly Ser Gly Val Lys Ile Ala Ile
    130                 135                 140

Val Asp Thr Gly Val Gln Ser Asn His Pro Asp Leu Ala Gly Lys Val
145                 150                 155                 160

Val Gly Gly Trp Asp Phe Val Asp Asn Asp Ser Thr Pro Gln Asp Gly
                165                 170                 175

Asn Gly His Gly Thr His Cys Ala Gly Ile Ala Ala Val Thr Asn
            180                 185                 190

Asn Ser Thr Gly Ile Ala Gly Thr Ala Pro Lys Ala Ser Ile Leu Ala
        195                 200                 205

Val Arg Val Leu Asp Asn Ser Gly Ser Gly Thr Trp Thr Ala Val Ala
    210                 215                 220

Asn Gly Ile Thr Tyr Ala Ala Asp Gln Gly Ala Lys Val Ile Ser Leu
225                 230                 235                 240

Ser Leu Gly Gly Thr Val Gly Asn Ser Gly Leu Gln Gln Ala Val Asp
                245                 250                 255

Tyr Ala Trp Asn Lys Gly Ser Val Val Val Ala Ala Ala Gly Asn Ala
            260                 265                 270

Gly Asn Thr Ala Pro Asn Tyr Pro Ala Tyr Tyr Ser Asn Ala Ile Ala

```
            275                 280                 285
Val Ala Ser Thr Asp Gln Asn Asp Asn Lys Ser Ser Phe Ser Thr Tyr
    290                 295                 300

Gly Ser Trp Val Asp Val Ala Ala Pro Gly Ser Ser Ile Tyr Ser Thr
305                 310                 315                 320

Tyr Pro Thr Ser Thr Tyr Ala Ser Leu Ser Gly Thr Ser Met Ala Thr
                325                 330                 335

Pro His Val Ala Gly Val Ala Gly Leu Leu Ala Ser Gln Gly Arg Ser
                340                 345                 350

Ala Ser Asn Ile Arg Ala Ala Ile Glu Asn Thr Ala Asp Lys Ile Ser
                355                 360                 365

Gly Thr Gly Thr Tyr Trp Ala Lys Gly Arg Val Asn Ala Tyr Lys Ala
            370                 375                 380

Val Gln Tyr
385

<210> SEQ ID NO 21
<211> LENGTH: 1164
<212> TYPE: DNA
<213> ORGANISM: Laceyella sacchari

<400> SEQUENCE: 21
atgaagaaac gcgtttccct catcgcttcc ttcgttttga tggcaagcgc cgccctgcct      60
tccgccattt tcgctgagga agtagatagc caagcgggta aactctatgc tccagggcaa     120
gtcgtggtga atacaaaga caatgcttcg gccagcgccg tcaaatctgc ccgcgccaaa      180
gccaacggta cagtcatgga gaaaacaaac aagctcggct tgaagtggt caaagtgaaa      240 ggctctgtgg aagcgaccat cgaaaagctg aaaaagacc ccaacgtgga atatgctgaa      300
cccaactact atctccacgc tacctacaca cctaacgatc cttacttcag ctcccgccaa     360
tacggcccac aaaaaatcca agcgccgcag gcatgggaca tcgctgaagg ctccggcgtg     420
aaaatcgcca tcgtcgacac cggggtgcaa tccaaccatc ccgacttggc cggtaaagta     480
gtgggcggtt gggacttcgt tgacaacgac tccactccgc aagatggcaa cggccacggt     540
acacactgcg ctggtatcgc cgcagcagtg accaacaaca gcaccgggat cgctggtact     600
gccccgaaag cgtcaatcct cgctgtgcgc gtgctggaca acagcggtag cggcacctgg     660
actgctgtcg ccaacggtat cacctatgct gcagaccaag cgctaaagt catcagcttg      720 agcttgggcg gcaccgttgg taactccggt ctgcaacaag ctgtcgacta cgcttggaac     780
aaaggttccg ttgtcgtggc cgcggctggt aacgccggca acaccgctcc taactatccc     840
gcttactatt ccaacgccat cgcggtagct tctactgacc aaaatgacaa caaatcctcc     900
ttctccactt acggttcctg ggtagatgta gctgctcctg gttccagcat ctattccacc     960 taccccgacca gcacctacgc ttccttgagc ggtacctcca tggctactcc tcacgtagct    1020
ggtgtggctg gactcttggc ttcccaaggc cgtagcgctt ccaatatccg cgccgccatt    1080
gaaaacaccg ccgacaaaat cagcggcact ggcacctact gggccaaagg acgcgtcaac    1140
gcttacaaag ctgttcagta ctaa                                           1164

<210> SEQ ID NO 22
<211> LENGTH: 1164
<212> TYPE: DNA
<213> ORGANISM: Thermoactinomyces sp. 16

<400> SEQUENCE: 22
```

-continued

```
atgaagaaac gcgtttccct catcgcttcc ttcgttttga tggcaagcgc cgccctgcct        60
tccgccattt tcgctgagga agtagatagc caagcgggta aactctatgc tccagggcaa       120
gtcgtggtga atacaaaga caatgcttcg gccagcgccg tcaaatctgc ccgcgccaaa       180
gccaacggta cagtcatgga gaaaaacaac aagctcggct ttgaagtggt caaagtgaaa       240
ggctctgtgg aagcgaccat cgaaaagctg aaaaaagacc ccaacgtgga atatgctgaa       300
cccaactact atctccacgc tacctacaca cctaacgatc cttacttcag ctcccgccaa       360
tacggcccac aaaaaatcca agcgccgcag gcatgggaca tcgctgaagg ctccggcgtg       420
aaaatcgcca tcgtcgacac cggggtgcaa tccaaccatc ccgacttggc cggtaaagta       480
gtgggcggtt gggacttcgt tgacaacgac tccactccgc aagatggcaa cggccacggt       540
acacactgcg ctggtatcgc cgcagcagtg accaacaaca gcaccgggat cgctggtact       600
gccccgaaag cgtcaatcct cgctgtgcgc gtgctggaca cagcggtag cggcacctgg       660 actgctgtcg ccaacggtat cacctatgct gcagaccaag gcgctaaagt catcagcttg       720
agcttgggcg gcaccgttgg taactccggt ctgcaacaag ctgtcgacta cgcttggaac       780
aaaggttccg ttgtcgtggc cgcggctggt aacgccggca acaccgctcc taactatccc       840
gcttactatt ccaacgccat cgcggtagct tctactgacc aaaatgacaa caaatcctcc       900
ttctccactt acggttcctg ggtagatgta gctgctcctg gttccagcat ctattccacc       960
tacccgacca gcacctacgc ttccttgagc ggtacctcca tggctactcc tcacgtagct      1020
ggtgtggctg gactcttggc ttcccaaggc cgtagcgctt ccaatatccg cgccgccatt      1080
gaaaacaccg ccgacaaaat cagcggcact ggcacctact gggccaaagg acgcgtcaac      1140
gcttacaaag ctgttcagta ctaa                                              1164
```